(12) United States Patent
Wagner

(10) Patent No.: US 10,973,841 B2
(45) Date of Patent: Apr. 13, 2021

(54) COMPOSITIONS FOR THE TREATMENT OF SKIN CONDITIONS

(71) Applicant: Forte Subsidiary, Inc., Torrance, CA (US)

(72) Inventor: Paul Wagner, Torrance, CA (US)

(73) Assignee: FORTE SUBSIDIARY, INC., Torrance, CA (US)

( * ) Notice: Subject to any disclaimer, the term of this patent is extended or adjusted under 35 U.S.C. 154(b) by 0 days.

(21) Appl. No.: 16/401,986

(22) Filed: May 2, 2019

(65) Prior Publication Data

US 2019/0343856 A1 Nov. 14, 2019

Related U.S. Application Data

(60) Provisional application No. 62/703,737, filed on Jul. 26, 2018, provisional application No. 62/670,341, filed on May 11, 2018.

(51) Int. Cl.

| | | |
|---|---|---|
| A61K 31/708 | (2006.01) | |
| A61K 31/16 | (2006.01) | |
| A61K 31/121 | (2006.01) | |
| A61K 31/201 | (2006.01) | |
| A61K 9/00 | (2006.01) | |
| A61K 31/336 | (2006.01) | |
| A61K 31/685 | (2006.01) | |
| A61K 38/06 | (2006.01) | |
| A61P 17/06 | (2006.01) | |
| A61K 31/565 | (2006.01) | |

(52) U.S. Cl.
CPC .......... *A61K 31/708* (2013.01); *A61K 9/0014* (2013.01); *A61K 31/121* (2013.01); *A61K 31/16* (2013.01); *A61K 31/201* (2013.01); *A61K 31/336* (2013.01); *A61K 31/565* (2013.01); *A61K 31/685* (2013.01); *A61K 38/06* (2013.01); *A61P 17/06* (2018.01)

(58) Field of Classification Search
CPC ...... A61P 17/06; A61K 31/708; A61K 31/121
See application file for complete search history.

(56) References Cited

U.S. PATENT DOCUMENTS

| | | | |
|---|---|---|---|
| 3,832,253 | A | 8/1974 | Di et al. |
| 3,854,480 | A | 12/1974 | Zaffaroni |
| 4,452,775 | A | 6/1984 | Kent |
| 4,667,014 | A | 5/1987 | Nestor, Jr. et al. |
| 4,748,034 | A | 5/1988 | De Rham |
| 4,829,000 | A | 5/1989 | Kleinman et al. |
| 5,239,660 | A | 8/1993 | Ooi |
| 6,218,371 | B1 | 4/2001 | Krieg et al. |
| 6,974,585 | B2 | 12/2005 | Askill |
| 8,481,299 | B2 | 7/2013 | Gueniche et al. |
| 9,173,910 | B2 | 11/2015 | Kaplan et al. |
| 10,195,236 | B2 * | 2/2019 | Myles .................. A61P 17/04 |
| 10,206,957 | B2 | 2/2019 | Myles et al. |
| 10,293,005 | B2 | 5/2019 | Myles et al. |
| 2012/0165357 | A1 | 6/2012 | Hung et al. |
| 2013/0121968 | A1 | 5/2013 | Quay |
| 2013/0251682 | A1 * | 9/2013 | Sprenger ................. A23L 33/40 |
| | | | 424/93.4 |
| 2013/0273144 | A1 | 10/2013 | Maj et al. |
| 2016/0192580 | A1 | 7/2016 | Wendte et al. |
| 2016/0235792 | A1 | 8/2016 | Berry et al. |
| 2016/0317653 | A1 | 11/2016 | Cook et al. |
| 2017/0202889 | A1 | 7/2017 | Lang et al. |
| 2018/0325968 | A1 | 11/2018 | Morris et al. |
| 2019/0076486 | A1 | 3/2019 | Myles et al. |
| 2019/0142873 | A1 | 5/2019 | Myles et al. |
| 2019/0142874 | A1 | 5/2019 | Myles et al. |
| 2019/0167735 | A1 | 6/2019 | Myles et al. |
| 2019/0175667 | A1 | 6/2019 | Myles et al. |
| 2019/0192580 | A1 | 6/2019 | Myles et al. |
| 2020/0254029 | A1 | 8/2020 | Myles et al. |

FOREIGN PATENT DOCUMENTS

| | | |
|---|---|---|
| EP | 1786445 A2 | 5/2007 |
| JP | 2006131622 A | 5/2006 |
| WO | WO-9510999 A1 | 4/1995 |
| WO | WO-03033660 A2 | 4/2003 |
| WO | WO-03047533 A2 | 6/2003 |
| WO | WO-2006036406 A2 | 4/2006 |
| WO | WO-2006048747 A1 | 5/2006 |

(Continued)

OTHER PUBLICATIONS

Adjide et al. A sensitive, specific and predictive isolation medium developed for Stenotrophomonas maltophilia study in healthcare settings. Pathol Biol (Paris) 58(1):11-7 (English Abstract) (2010).

Cyzeska et al. Culture Medium for Selective Isolation and Enumeration of Gram-Negative Bacteria from Ground Meats. Appl Environ Microbiol. 42(2):303-307 (1981).

Dekio et al. Characterization of skin microbiota in patients with atopic dermatitis and in normal subjects using 16S rRNA gene-based comprehensive analysis. J Med Microbiol 56:1675-1683 (2007).

Furuhata et al. Characteristics of a Pink-Pigmented Bacterium Isolated from Biofilm in a Cooling Tower in Tokyo, Japan. Microbiol Immunol 51(6):637-641 (2007).

Jewelewicz et al. Modified rapid deployment hemostat bandage reduces blood loss and mortality in coagulopathic pigs with severe liver injury. J Trauma 55:275-281 (2003).

(Continued)

*Primary Examiner* — Pancham Bakshi
(74) *Attorney, Agent, or Firm* — Wilson Sonsini Goodrich & Rosati

(57) ABSTRACT

Described herein are methods and compositions for the treatment of skin conditions associated the dysbiosis. Further described herein is the use of metabolites for treatment of dysregulated microbiota in a subject. Such metabolites can be produced by microorganisms present in a higher abundance in the skin of healthy subjects as compared to the skin of a subject having dysbiosis of the skin. In addition, compositions and methods provided herein describe the use of metabolites as part of a combination therapy.

17 Claims, 1 Drawing Sheet

Specification includes a Sequence Listing.

(56) References Cited

FOREIGN PATENT DOCUMENTS

| WO | WO-2012150269 A1 | 11/2012 |
|---|---|---|
| WO | WO-2013153358 A1 | 10/2013 |
| WO | WO-2015160911 A2 | 10/2015 |
| WO | WO-2016172196 A1 | 10/2016 |
| WO | WO-2017184601 A1 | 10/2017 |
| WO | WO-2020023072 A1 | 1/2020 |

OTHER PUBLICATIONS

Kim et al. Two Cases of Bacteremia Due to Roseomonas Mucosa. Annals of Laboratory Medicine 36: 367-370 (2016).
Mankowska-Wierzbicka et al. The Microbiome and Dermatological Diseases. Postepy Hig Med Dosw 69:978-985 (2015).
O'Doherty et al. Development of nalidixic acid amphotericin B vancomycin (NAV) medium for the isolation of Campylobacter ureolyticus from the stools of patients presenting with acute gastroenteritis. Br J Biomed Sci 71(1):6-12 (2014).
PCT/US2019/030444 International Search Report and Written Opinion dated Aug. 30, 2019.
Romano-Bertrand et al. Skin Microbiota is the Main Reservoir of Roseomonas Mucosa, an Emerging Opportunistic Pathogen so Far Assumed to be Environmental. Clinical Microbiology and Infection 22:737e1-737e7 (2016).
Truant et al. *Methylobacterium* Species: An Increasingly Important Opportunistic Pathogen. Laboratory Medicine 29(11):704-710 (1998).
U.S. Appl. No. 16/184,498 Office Action dated Oct. 11, 2019.
U.S. Appl. No. 16/244,903 Office Action dated Dec. 4, 2019.
U.S. Appl. No. 16/244,903 Office Action dated Sep. 9, 2019.
U.S. Appl. No. 16/249,721 Office Action dated Aug. 16, 2019.
U.S. Appl. No. 16/249,721 Office Action dated Nov. 18, 2019.
U.S. Appl. No. 16/271,552 Office Action dated Aug. 23, 2019.
U.S. Appl. No. 16/271,577 Office Action dated Oct. 11, 2019.
U.S. Appl. No. 16/288,630 Office Action dated Oct. 11, 2019.
U.S. Appl. No. 16/386,736 Office Action dated Feb. 12, 2020.
U.S. Appl. No. 16/522,333 Office Action dated Nov. 5, 2019.
U.S. Appl. No. 16/522,357 Office Action dated Oct. 17, 2019.
U.S. Appl. No. 16/522,379 Office Action dated Jan. 9, 2020.
U.S. Appl. No. 16/522,379 Office Action dated Oct. 28, 2019.
Abbasi. Are Bacteria Transplants the Future of Eczema Therapy? JAMA pp. E1-E2 (Aug. 29, 2018).
Asher et al. Worldwide time trends in the prevalence of symptoms of asthma, allergic rhinoconjunctivitis, and eczema in childhood: ISAAC Phases One and Three repeat multicountry cross-sectional surveys. Lancet 368:733-743 (2006).
Avis. Chapter 87: Parenteral Preparations. Remington: The Science and Practice of Pharmacy, 19th Ed. (Easton, PA: Mack Publishing Co.) (p. 1530) (1995).
Bantz et al. The Atopic March: Progression from Atopic Dermatitis to Allergic Rhinitis and Asthma. J Clin Cell Immunol 5(2):202 (2014).
Barnes et al. An update on the genetics of atopic dermatitis: scratching the surface in 2009. J Allergy Clin Immunol 125:16-31 (2010).
Bieber. Atopic dermatitis. Ann Dermatol. 22:125-37 (2010).
Bieber et al. Pathogenesis of atopic dermatitis: New developments. Curr Allergy Asthma Rep.9:291-4 (2009).
Bilal et al. Pattern of Bacterial Colonization of Atopic Dermatitis in Saudi Children. J Clin Diagn Res. 7(9):1968-1970 (2013).
Bin et al. Genetic and epigenetic studies of atopic dermatitis. Allergy Asthma Clin Immunol 12:52 (2016).
Bogdanffy et al. Metabolism of Dibasic Esters by Rat Natal Mucosal Carboxylesterase. Drug Metab Dispos 19(1):124-129 (1991).
Boguniewicz et al. Recent insights into atopic dermatitis and implications for management of infectious complications. J Allergy Clin Immunol 125(1):4-19 (2010).
Boguniewicz et al. The ABC's of managing patients with severe atopic dermatitis. J Allergy Clin Immunol 132(2):511-2.e5 (2013).
Brauweiler et al. The cytokines increase *Staphylococcus aureus* alpha toxin-induced keratinocyte death through the signal transducer and activator of transcription 6 (STAT6). J Invest Dermatol 134(8):2114-2121 (2014).
Charman et al. The patient-oriented eczema measure: Development and initial validation of a new tool for measuring atopic eczema severity from the patients' perspective. Arch Dermatol. 140:1513-9 (2004).
Co-pending U.S. Appl. No. 16/386,736, filed Apr. 17, 2019.
Co-pending U.S. Appl. No. 16/522,333, filed Jul. 25, 2019.
Co-pending U.S. Appl. No. 16/522,357, filed Jul. 25, 2019.
Co-pending U.S. Appl. No. 16/522,379, filed Jul. 25, 2019.
Czarnowicki et al. Novel concepts of prevention and treatment of atopic dermatitis through barrier and immune manipulations with implications for the atopic march. J Allergy Clin Immunol 139(6):1723-1734 (2017).
Dé et al. Clinical significance of *Roseomonas* species isolated from catheter and blood samples: analysis of 36 cases in patients with cancer. Clin Infect Dis 38(11):1579-1584 (2004).
Di Nardo et al. Ceramide and cholesterol composition of the skin of patients with atopic dermatitis. Acta Derm Venereol 78(1):27-30 (1998).
Dinulos et al. New science and treatment paradigms for atopic dermatitis. Curr Opin Pediatr 30(1):161-168 (2018).
Dolgin. First eczema biologic debuts but price could restrict use. Nat Biotechnol 35(5):391-392 (2017).
Dréno et al. Microbiome in healthy skin, update for dermatologists. J Eur Acad Dermatol Venereol 30(12):2038-2047 (2016).
Eichenfield et al. Current guidelines for the evaluation and management of atopic dermatitis: A comparison of the Joint Task Force Practice Parameter and American Academy of Dermatology guidelines. J Allergy Clin Immunol 139(4S):S49-S57 (2017).
Eichenfield et al. Guidelines of Care for the Management of Atopic Dermatitis: Part 2: Management and Treatment of Atopic Dermatitis with Topical Therapies. J Am Acad Dermatol 71(1):116-132 (2014).
Fernandez. Five cases of Pantoea septica related catheter infections. Abstract E0270, presented at 28th ECCMID, Madrid, Spain, Apr. 21-24, 2018 (1 pg.) (2018).
Follin et al. A skin chamber technique as a human model for studies of aseptic inflammatory reactions. Method Mol Biol 412:333-346 (2007).
Gerding et al. Administration of Spores of Nontoxigenic Clostridium difficile Strain M3 for Prevention of Recurrent C difficile Infection: A Randomized Clinical Trial. JAMA 313(17):1719-1727 (2015).
Gittler et al. Bathing and Associated Treatment in Atopic Dermatitis. Am J Clin Dermatol 18:45-57 (2017).
Grice et al. The Skin Microbiome. Nature 9:244-253 (2011).
Gueniche et al. Effects of nonpathogenic gram-negative bacterium Vitreoscilla filiformis lysate on atopic dermatitis: a prospective, randomized, double-blind, placebo-controlled clinical study. Br J Dermatol 159:1357-1363 (2008).
Hanifin et al. Diagnostic features of atopic dermatitis. Acta Derm Venereol. 92:44-7 (1980).
Hanifin et al. The eczema area and severity index (EASI): assessment of reliability in atopic dermatitis. EASI Evaluator Group. Exp Dermatol. 10:11-8 (2001).
Henderson et al. The burden of disease associated with filaggrin mutations: A population-based, longitudinal birth cohort study. J Allergy Clin Immunol 121(4):872-877.e9 (2008).
Hon et al. Barrier repair therapy in atopic dermatitis: an overview. Am J Clin Dermatol 14(5):389-399 (2013).
Hsu et al. Intermediate phenotypes in patients with autosomal dominant hyper-IgE syndrome caused by somatic mosaicism. J Allergy Clin Immunol 131(6):1586-1593 (2013).
Hwang et al. Prevalence of atopic dermatitis, allergic rhinitis and asthma in Taiwan: a national study 2000 to 2007. Acta Derma Venereol 90(6):589-594 (2010).
Inami et al. Surfactant-induced Chronic Pruritus: Role of L-Histidine Decarboxylase Expression and Histamine Production in Epidermis. Acta Derm Venereol 94:645-650 (2014).
Inoshima et al. A *Staphylococcus aureus* pore-forming toxin subverts the activity of ADAM10 to cause lethal infection in mice. Nature 17(10):1310-1315 (2011).

(56) References Cited

OTHER PUBLICATIONS

Janmohamed et al. The proactive wet-wrap method with diluted corticosteroids versus emollients in children with atopic dermatitis: a prospective, randomized, double-blind, placebo-controlled trial. J Am Acad Dermatol 70(6):1076-1082 (2014).
Jensen et al. Impaired Sphingomyelinase Activity and Epidermal Differentiation in Atopic Dermatitis. J Invest Dermatol 122(6):1423-1431 (2004).
Kobayashi et al. Dysbiosis and *Staphylococcus aureus* Colonization Drives Inflammation in Atopic Dermatitis. Immunity 42(4):756-766 (2015).
Kolls et al. Cytokine-mediated regulation of antimicrobial proteins. Nat Rev Immunol 8(11):829-835 (2008).
Kong et al. Temporal shifts in the skin microbiome associated with disease flares and treatment in children with atopic dermatitis. Genome Res 22(5):850-859 (2012).
Krämer et al. Seasonality in symptom severity influenced by temperature or grass pollen: results of a panel study in children with eczema. J Invest Dermatol 124(3):514-523 (2005).
Kubo et al. Epidermal barrier dysfunction and cutaneous sensitization in atopic diseases. J Clin Invest 122(2):440-447 (2012).
Latvala et al. Trends in prevalence of asthma and allergy in Finnish young men: nationwide study, 1966-2003. BMJ 330(7501):1186-1187 (2005).
Lau et al. A rapid matrix-assisted laser desorption ionization-time of flight mass spectrometry-based method for single-plasmid tracking in an outbreak of carbapenem-resistant Enterobacteriaceae. J Clin Microbiol 52:2804-2812 (2014).
Lau et al. Development of a clinically comprehensive database and a simple procedure for identification of molds from solid media by matrix-assisted laser desorption ionization-time of flight mass spectrometry. J Clin Microbiol 51:828-834 (2013).
Leloup et al. Outpatient Home-based Wet Wrap Dressings with Topical Steroids with Children with Severe Recalcitrant Atopic Dermatitis: A Feasibility Pilot Study. Pediatr Dermatol 32(4):e177-178 (2015).
Lewis-Jones. Quality of life and childhood atopic dermatitis: the misery of living with childhood eczema. Int J Clin Pract 60(8):984-992 (2006).
Li et al. Altered composition of epidermal lipids correlates with *Staphylococcus aureus* colonization status in atopic dermatitis. Br J Dermatol 177(4):e125-e127 (2017).
Li et al. Topical vitamin D3 and low-calcemic analogs induce thymic stromal lymphopoietin in mouse keratinocytes and trigger an atopic dermatitis. PNAS USA 103(31):11736-11741 (2006).
Lyons et al. Atopic dermatitis in children: clinical features, pathophysiology, and treatment. Immunol Allergy Clin North Am 35:161-183 (2015).
Margolis et al. Persistence of mild to moderate atopic dermatitis. JAMA Dermatol. 150(6):593-600 (2014).
Mennini et al. Two Phase 3 Trials of Dupilumab versus Placebo in Atopic Dermatitis. N Engl J Med 376(11):1090 (2017).
Michon et al. Bacteremia due to imipenem-resistant Roseomonas mucosa in a child with acute lymphoblastic leukemia. J Pediatr Hematol Oncol. 36(3):e165-168 (2014).
Miller et al. Vitamin D and innate immunity. Dermatol Ther 23:13-22 (2010).
Miyamoto-Shinohara et al. Survival of freeze-dried bacteria. J Gen Appl Microbiol 54(1):9-24 (2008).
Msika et al. New emollient with topical corticosteroid-sparing effect in treatment of childhood atopic dermatitis: SCORAD and quality of life improvement. Pediatr Dermatol 25(6):606-612 (2008).
Muthuri et al. Impact of neuraminidase inhibitors on influenza A(H1N1)pdm09-related pneumonia: an individual participant data meta-analysis. Influenza Other Respir Viruses 10(3):192-204 (2016).
Myles et al. A method for culturing Gram-negative skin microbiota. BMC Microbiol 16:60 (2016).
Myles et al. First-in-human topical microbiome transplantation with Roseomonas mucosa for atopic dermatitis. JCI Insight 3(9):e120608 (2018).
Myles et al. Signaling via the IL-20 receptor inhibits cutaneous production of IL-1 beta and IL-17A to promote infection with methicillin-resistant *Staphylococcus aureus*. Nature Immunol 14(8):804-811 (2013).
Myles et al. *Staphylococcus aureus*: an introduction. Semin Immunopathol 34(2):181-184 (2012).
Myles et al. Transplantation of human skin microbiota in models of atopic dermatitis. JCI Insight 1(10):e86955 (2016).
Myles. Fast food fever: reviewing the impacts of the Western diet on immunity. Nutrition Journal 13:61 (2014).
Nakamura et al. *Staphylococcus* delta-toxin induces allergic skin disease by activating mast cells. Nature 503(7476):397-401 (2013).
Nakatsuji et al. Antimicrobials from human skin commensal bacteria protect against *Staphylococcus aureus* and are deficient in atopic dermatitis. Sci Transl Med 9(378):eaa4680.
Neuber et al. Treatment of atopic eczema with oral mycophenolate mofetil. Br J Dermatol 143(2):385-391 (2000).
Ngugi et al. Effects of Bacterial Vaginosis-Associated Bacteria and Sexual Intercourse on Vaginal Colonization With the Probiotic Lactobacillus crispatus CTV-05. Sex Transm Dis 38(11):1020-1027 (2011).
Nygaard et al. Emerging Treatment Options in Atopic Dermatitis: Systemic Therapies. Dermatology 233:344-357 (2017).
Olle. Medicines from microbiota. Nat Biotechnol 31(4):309-315 (2013).
Pajno et al. Sublingual immunotherapy in mite-sensitized children with atopic dermatitis: a randomized, double-blind, placebo-controlled study. J Allergy Clin Immunol 120(1):164-170 (2007).
Park et al. The Pathogenetic Effect of Natural and Bacterial Toxins on Atopic Dermatitis. Toxins (Basel) 9(1):E3 (19 pgs) (2016).
PCT/US2017/028133 International Search Report and Written Opinion dated Sep. 4, 2017.
PCT/US2018/059073 International Search Report and Written Opinion dated Feb. 15, 2019.
PCT/US2019/027912 International Search Report and Written Opinion dated Jul. 17, 2019.
PCT/US2019/030444 Invitation to Pay Additional Fees dated Jul. 5, 2019.
Pirie et al. Anemia and iron-restricted erythropoiesis in traumatic critical illness. J Trauma Acute Care Surg 80(3):538-545 (2016).
Proctor et al. Small colony variants: a pathogenic form of bacteria that facilitates persistent and recurrent infections. Microbiology 4:295-305 (2006).
Pullmannová et al. Effects of sphingomyelin/ceramide ratio on the permeability and microstructure of model stratum corneum lipid membranes. Biochimica et Biophysica Acta 1838:2115-2126 (2014).
Pyun. Natural history and risk factors of atopic dermatitis in children. Allergy Asthma Immunol Res 7(2):101-105 (2015).
Ramakrishnan et al. Skin and Soft Tissue Infections. Am. Fam. Physician. 92(6):474-483 (2015).
Reilly. Chapter 80: Pharmaceutical Necessities. Remington: The Science and Practice of Pharmacy, 19th Ed. (Easton, PA: Mack Publishing Co.) (pp. 1380-1404) (1995).
Rietschel et al. Chapter 5: Structure and conformation of the lipid a component of lipopolysaccharides. Handbook of Endotoxin 1:187-214, eds. R. Proctor and E. Rietschel, Elsevier, Amsterdam (1984).
Rosenfeldt et al. Effect of probiotic Lactobacillus strains in children with atopic dermatitis. J Allergy Clin Immunol 111(2):389-395 (2003).
Rudmik et al. Medical Therapies for Adult Chronic Sinusitis: A Systematic Review. JAMA 314(9):926-939 (2015).
Schauber et al. The vitamin D pathway: a new target for control of the skin's immune response? Exp Dermatol 17(8):633-639 (2008).
Schlievert et al. Secreted virulence factor comparison between methicillin-resistant and methicillin-sensitive *Staphylococcus aureus*, and its relevance to atopic dermatitis. J Allergy Clin Immunol 125(1):39-49 (2010).
Shi. The Gut and Skin Microbiome in Atopic Dermatitis. AIHM Annual Conference 2017 (18 pgs) (2017).
Silverberg et al. Association between severe eczema in children and multiple comorbid conditions and increased healthcare utilization. Pediatr Allergy Immunol. 24:476-86 (2013).

(56) References Cited

OTHER PUBLICATIONS

Silverberg. Public Health Burden and Epidemiology of Atopic Dermatitis. Dermatol Clin 35:283-289 (2017).
Sipsas et al. Septic arthritis due to Roseomonas mucosa in a rheumatoid arthritis patient receiving infliximab therapy. Diagn Microbiol Infect Dis 55(4):343-345 (2006).
Spanier et al. The associations of triclosan and paraben exposure with allergen sensitization and wheeze in children. Allergy Asthma Proc 35(6):475-481 (2014).
Stevenson et al. Evaluation of matrix-assisted laser desorption ionization-time of flight mass spectrometry for identification of clinically important yeast species. J Clin Microbiol 48:3482-3486 (2010).
Tan et al. Pathogenicity of Moraxella osloensis, a Bacterium Associated with the Nematode Phasmarhabditis hermaphrodita, to the Slug Deroceras reticulatum. Applied and Environmental Microbiology 67(11):5010-5016 (2001).
Trüper. Etymology in Nomenclature of Procaryotes. Bergey's Manual of Systemic Bacteriology, vol. Two, The Proteobaceria, Part 3, Springer Science & Business Media (pp. 88-99) (2001).
U.S. Appl. No. 15/939,066 Office Action dated Sep. 19, 2018.
U.S. Appl. No. 16/014,971 Office Action dated Sep. 7, 2018.
U.S. Appl. No. 16/184,498 Office Action dated May 15, 2019.
U.S. Appl. No. 16/271,552 Office Action dated Mar. 18, 2019.
U.S. Appl. No. 16/271,577 Office Action dated May 9, 2019.
U.S. Appl. No. 16/288,360 Office Action dated May 30, 2019.
Wang et al. New insights into T cells and their signature cytokines in atopic dermatitis. IUBMB Life 67(8):601-610 (2015).
Wang et al. Thymic stromal lymphopoietin signaling in CD4(+) T cells is required for TH2 memory. J Allergy Clin Immunol 135:781-791.e3 (2015).
Weston et al. Effects of probiotics on atopic dermatitis: a randomised controlled trial. Arch Dis Child 90(9):892-897 (2005).
Williams et al. Is eczema really on the increase worldwide? J Allergy Clin Immunol. 121:947-54.e15 (2008).
Williams et al. The natural history of childhood eczema: observations from the British 1958 birth cohort study. Br J Dermatol 139(5):834-839 (1998).
Wollenberg et al. Current aspects of innate and adaptive immunity in atopic dermatitis. Clin Rev Allergy Immunol 33(1-2):35-44 (2007).
Worth et al. Food allergy and atopic eczema. Clin Rev Allergy Immunol 10(3):226-230 (2010).
Youn et al. Clinical Performance of a Matrix-Assisted Laser Desorption Ionization—Time of Flight Mass Spectrometry Method for Detection of Certain blaKPC-Containing Plasmids. J Clin Microbiol 54(1):35-42 (2015).
Zhang et al. Characterization of the skin fungal microbiota in patients with atopic dermatitis and in healthy subjects. Microbiol Immunol 55:625-632 (2011).
Zuberbier et al. Patient perspectives on the management of atopic dermatitis. J Allergy Clin Immunol. 118:226-32 (2006).
Hanifin et al. Intermittent dosing of fluticasone propionate cream for reducing the risk of relapse in atopic dermatitis patients. Br J Dermatol 147:528-537 (2002).
U.S. Appl. No. 16/184,498 Office Action dated Jun. 19, 2020.
U.S. Appl. No. 16/386,736 Office Action dated Apr. 15, 2020.
U.S. Appl. No. 16/522,333 Office Action dated Jul. 7, 2020.
U.S. Appl. No. 16/522,357 Office Action dated Jul. 7, 2020.
U.S. Appl. No. 16/244,903 Office Action dated Oct. 1, 2020.
U.S. Appl. No. 16/288,630 Office Action dated Aug. 14, 2020.

\* cited by examiner

COMPOSITIONS FOR THE TREATMENT OF SKIN CONDITIONS

This application claims benefit of U.S. Provisional Application No. 62/670,341, filed on May 11, 2018, and U.S. Provisional Application No. 62/703,737, filed on Jul. 26, 2018, both of which are incorporated herein by reference in their entirety.

SEQUENCE LISTING

The instant application contains a Sequence Listing which has been submitted in ASCII Format via EFS-Web and is hereby incorporated by reference in its entirety. Said ASCII copy, created on Apr. 22, 2019, is named 53654-704_201_SL.txt and is 2,122 bytes in size.

BACKGROUND

Dysbiosis of the skin microbiome is associated with a variety of diseases where the skin barrier is disrupted and inflammation at the site of disruption may be increased as well. For example, in the case of atopic dermatitis, the skin microbiome of healthy subjects is significantly different from that of atopic dermatitis subjects. Symptoms of atopic dermatitis are often attributed to loss of commensal diversity. Microbiota dysfunction is also a feature of atopic dermatitis pathology. Overgrowth and infection of *Staphylococcus aureus* are contributors and consequences of immune imbalance and poor barrier function. Antibiotic treatments that mitigate growth of *S. aureus* can improve atopic dermatitis symptoms, but often cannot normalize the underlying pathology. Thus, there is a need for improved therapies for treatment of skin diseases associated with dysbiosis.

BRIEF SUMMARY

Provided herein are pharmaceutical compositions comprising: a metabolite, wherein the metabolite is present in an amount sufficient to reduce skin dysbiosis in a subject in need thereof, and wherein the metabolite is produced from a species of gram-negative bacteria that is more highly abundant in skin from a subject that does not have skin dysbiosis as compared to abundance of the species in skin from a subject having skin dysbiosis; and a pharmaceutically-acceptable carrier. Further provided herein are compositions, wherein the species of gram-negative bacteria comprises a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa*, *Pseudomonas luteola*, or *Pseudomonas oryzihabitans*. Further provided herein are compositions, wherein the subject has atopic dermatitis, rosacea, or psoriasis. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine (18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, comprising a plurality of different metabolites produced from the same or different species of gram-negative bacteria that are more highly abundant in skin from the subject that does not have atopic dermatitis as compared to abundance of the species in skin from the subject having atopic dermatitis. Further provided herein are compositions, wherein the composition is in a topical, rectal, or oral dosage form. Further provided herein are compositions, wherein the topical dosage form is a liquid, cream, gel, or foam. Provided herein are methods for treatment of skin dysbiosis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a metabolite, wherein the metabolite is present in an amount sufficient to reduce atopic dermatitis in a subject in need thereof, and wherein the metabolite is produced from a species of gram-negative bacteria that is more highly abundant in skin from a subject that does not have atopic dermatitis as compared to abundance of the species in skin from a subject having atopic dermatitis; and a pharmaceutically-acceptable carrier. Further provided herein are compositions, wherein the species of gram-negative bacteria comprises a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine (18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, comprising a plurality of different metabolites produced from the same or different species of gram-negative bacteria that are more highly abundant in skin from the subject that does not have atopic dermatitis as compared to abundance of the species in skin from the subject having atopic dermatitis. Further provided herein are compositions, wherein the composition is in a topical, rectal, or oral dosage form. Further provided herein are compositions, wherein the topical dosage form is a liquid, cream, gel, or foam. Provided herein are methods for treatment of atopic dermatitis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a first therapeutic agent, wherein the first therapeutic agent is a metabolite, wherein the metabolite is produced from a species of gram-negative bacteria that is more highly abundant in skin from a subject that does not have skin dysbiosis as compared to abundance of the species in skin from a subject having skin dysbiosis; and a second therapeutic agent, wherein the first therapeutic agent is present in an amount to enhance the second therapeutic agent in treatment of skin dysbiosis. Further provided herein are compositions, wherein the species of gram-negative bacteria comprises a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the subject has atopic dermatitis, rosacea, or psoriasis. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine (18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, comprising a plurality of different metabolites produced from the same or different species of gram-negative bacteria that are more highly abundant in skin from the subject that does not have atopic dermatitis as compared to abundance of the species in skin from the subject having atopic dermatitis. Further provided herein are compositions, wherein the second therapeutic agent is a microorganism, calcineurin inhibitor, antibody, small molecule, or steroid. Further provided herein are compositions, wherein the microorganism is a species of gram-negative bacteria. Further provided herein are compositions, wherein the species of gram-negative bacteria comprises a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the gram-negative bacteria are present in an amount of from $10^3$ to $10^{12}$ colony forming units. Further provided herein are compositions, wherein the composition is in a topical, rectal, or oral dosage form. Further provided herein are compositions, wherein the topical dosage form is a liquid, cream, gel, or foam. Provided herein are methods for treatment of skin dysbiosis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a first therapeutic agent, wherein the first therapeutic agent is a metabolite, wherein the metabolite is produced from a species of gram-negative bacteria that is more highly abundant in skin from a subject that does not have atopic dermatitis as compared to abundance of the species in skin from a subject having atopic dermatitis; and a second therapeutic agent, wherein the first therapeutic agent is present in an amount to enhance the second therapeutic agent in treatment of atopic dermatitis. Further provided herein are compositions, wherein the species of gram-negative bacteria comprises a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine(18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, comprising a plurality of different metabolites produced from the same or different species of gram-negative bacteria that are more highly abundant in skin from the subject that does not have atopic dermatitis as compared to abundance of the species in skin from the subject having atopic dermatitis. Further provided herein are compositions, wherein the second therapeutic agent is a microorganism, calcineurin inhibitor, antibody, small molecule, or steroid. Further provided herein are compositions, wherein the microorganism is a species of gram-negative bacteria. Further provided herein are compositions, wherein the species of gram-negative bacteria comprises a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the gram-negative bacteria are present in an amount of from $10^3$ to $10^{12}$ colony forming units. Further provided herein are compositions, wherein the composition is in a topical, rectal, or oral dosage form. Further provided herein are compositions, wherein the topical dosage form is a liquid, cream, gel, or foam. Provided herein are methods for treatment of atopic dermatitis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a metabolite, wherein the metabolite is present in an amount sufficient to reduce skin dysbiosis in a subject in need thereof, and wherein the metabolite is produced from a species of *Roseomonas* or a species of *Pseudomonas* that is more highly abundant in skin from a subject that does not have skin dysbiosis as compared to abundance of the species in skin from a subject having skin dysbiosis; and a second therapeutic agent, wherein the first therapeutic agent is present in an amount to enhance the second therapeutic agent in treatment of skin dysbiosis. Further provided herein are compositions, wherein the species of *Roseomonas* is *Roseomonas mucosa*. Further provided herein are compositions, wherein the species of *Pseudomonas* is *Pseudomonas aeruginosa, Pseudomonas luteola*, or *Pseudomonas oryzihabitans*. Further provided herein are compositions, wherein the subject has atopic dermatitis, rosacea, or psoriasis. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine (18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, wherein the second therapeutic agent is a wherein the second therapeutic agent is a microorganism, calcineurin inhibitor, antibody, small molecule, or steroid. Further provided herein are compositions, wherein the microorganism is a gram-negative bacteria. Further provided herein are compositions, wherein the gram-negative bacteria comprise a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the gram-negative bacteria are present in an amount of from $10^3$ to $10^{12}$ colony forming units. Further provided herein are compositions, wherein the composition is in a topical, rectal, or oral dosage form. Further provided herein are compositions, wherein the topical dosage form is a liquid, cream, gel, or foam. Provided herein are methods for treatment of skin dysbiosis, comprising: administering to a subject in need thereof a pharmaceutical composition provided herein. Further provided herein are methods, wherein the subject has atopic dermatitis, rosacea, or psoriasis. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a metabolite, wherein the metabolite is present in an amount sufficient to reduce atopic dermatitis in a subject in need thereof, and wherein the metabolite is produced from a species of *Roseomonas* or a species of *Pseudomonas* that is more highly abundant in skin from a subject that does not have atopic dermatitis as compared to abundance of the species in skin from a subject having atopic dermatitis; and a second therapeutic agent, wherein the first therapeutic agent is present in an amount to enhance the second therapeutic agent in treatment of skin dysbiosis. Further provided herein are compositions, wherein the species of *Roseomonas* is *Roseomonas mucosa*. Further provided herein are compositions, wherein the species of *Pseudomonas* is *Pseudomonas aeruginosa, Pseudomonas luteola*, or *Pseudomonas oryzihabitans*. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine(18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, wherein the second therapeutic agent is a wherein the second therapeutic agent is a microorganism, calcineurin inhibitor, antibody, small molecule, or steroid. Further provided herein are compositions, wherein the microorganism is a gram-negative bacteria. Further provided herein are compositions, wherein the gram-negative bacteria comprise a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the gram-negative bacteria are present in an amount of from $10^3$ to $10^{12}$ colony forming units. Further provided herein are compositions, wherein the composition is in a topical, rectal, or oral dosage form. Further provided herein are compositions, wherein the topical dosage form is a liquid, cream, gel, or foam. Provided herein are methods for treatment of atopic dermatitis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a first therapeutic agent, wherein the first therapeutic agent is a metabolite, wherein the metabolite is produced from a species of *Roseomonas* or a species of *Pseudomonas* that is more highly abundant in skin from a subject that does not have skin dysbiosis as compared to abundance of the species in skin from a subject having skin dysbiosis; and a second therapeutic agent, wherein the first therapeutic agent is present in an amount to enhance the second therapeutic agent in treatment of skin dysbiosis. Further provided herein are compositions, wherein the species of *Roseomonas* is *Roseomonas mucosa*. Further provided herein are compositions, wherein the species of *Pseudomonas* is *Pseudomonas aeruginosa, Pseudomonas luteola*, or *Pseudomonas oryzihabitans*. Further provided herein are methods, wherein the subject has atopic dermatitis, rosacea, or psoriasis. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine (18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, wherein the second therapeutic agent is a wherein the second therapeutic agent is a microorganism, calcineurin inhibitor, antibody, small molecule, or steroid. Further provided herein are compositions, wherein the microorganism is a gram-negative bacteria. Further provided herein are compositions, wherein the gram-negative bacteria comprise a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the gram-negative bacteria are present in an amount of from $10^3$ to $10^{12}$ colony forming units. Further provided herein are compositions, wherein the composition is in a topical, rectal, or oral dosage form. Further provided herein are compositions, wherein the topical dosage form is a liquid, cream, gel, or foam. Provided herein are methods for treatment of atopic dermatitis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

Provided herein are pharmaceutical compositions comprising: a first therapeutic agent, wherein the first therapeutic agent is a metabolite, wherein the metabolite is produced from a species of *Roseomonas* or a species of *Pseudomonas* that is more highly abundant in skin from a subject that does not have atopic dermatitis as compared to abundance of the species in skin from a subject having atopic dermatitis; and a second therapeutic agent, wherein the first therapeutic agent is present in an amount to enhance the second therapeutic agent in treatment of atopic dermatitis. Further provided herein are compositions, wherein the species of *Roseomonas* is *Roseomonas mucosa*. Further provided herein are compositions, wherein the species of *Pseudomonas* is *Pseudomonas aeruginosa, Pseudomonas luteola*, or *Pseudomonas oryzihabitans*. Further provided herein are compositions, wherein the metabolite is N4-acetylaminobutanal, 5-ethylpentadecane-2,4-dione, ricinoleic acid methyl ester, trenbolone acetate, or N-(2-hydroxyethyl)-11(12)-epoxy-5Z,8Z,14Z-eicosatrienamide. Further provided herein are compositions, wherein the metabolite is a lipid. Further provided herein are compositions, wherein the lipid comprises phosphatidylethanolamine 36:2, phosphatidylcholine 37:0, phosphatidylcholine 37:2, phosphatidylcholine 38:2, phosphatidylcholine(18:2(9Z,12Z)/18:0), phosphatidylethanolamine 14:0/20:1, phosphatidylethanolamine 22:1/14:1, phosphatidylethanolamine 36:2, or 8-keto palmitic acid. Further provided herein are compositions, wherein the metabolite is a peptide. Further provided herein are compositions, wherein the peptide comprises Tyr-Leu-Arg. Further provided herein are compositions, wherein the metabolite is a sugar. Further provided herein are compositions, wherein the sugar comprises maltopentaose. Further provided herein are compositions, wherein the metabolite is a nucleotide. Further provided herein are compositions, wherein the nucleotide comprises 2'-deoxyguanosine 5'-monophosphate. Further provided herein are compositions, wherein the second therapeutic agent is a wherein the second therapeutic agent is a microorganism, calcineurin inhibitor, antibody, small molecule, or steroid. Further provided herein are compositions, wherein the microorganism is a gram-negative bacteria. Further provided herein are compositions, wherein the gram-negative bacteria comprise a *Roseomonas* genus bacterium. Further provided herein are compositions, wherein the *Roseomonas* genus bacterium is *Roseomonas mucosa*. Further provided herein are compositions, wherein the species of gram-negative bacteria comprises a *Pseudomonas* genus bacterium. Further provided herein are compositions, wherein the *Pseudomonas* genus bacterium is *Pseudomonas aeruginosa, Pseudomonas luteola*, or *Pseudomonas oryzihabitans*. Further provided herein are compositions, wherein the gram-negative bacteria are present in an amount of from $10^3$ to $10^{12}$ colony forming units. Further provided herein are compositions, wherein the composition is in a topical, rectal, or oral dosage form. Further provided herein are compositions, wherein the topical dosage form is a liquid, cream, gel, or foam. Provided herein are methods for treatment of atopic dermatitis, comprising: administering to a subject in need thereof a pharmaceutical composition provided herein. Further provided herein are methods, wherein the pharmaceutical composition is topically, orally, or rectally administered. Further provided herein are methods, wherein the pharmaceutical composition is topically administered by spraying. Further provided herein are methods, wherein the pharmaceutical composition is administered to the subject at least two times per a week. Further provided herein are methods, wherein the pharmaceutical composition is administered to the subject every other day over a week. Further provided herein are methods, wherein the pharmaceutical composition is administered to the subject once a day. Further provided herein are methods, wherein the subject is an adult. Further provided herein are methods, wherein the subject is a child. Further provided herein are methods, wherein the subject is an infant. Further provide herein are pharmaceutical compositions wherein the at least one strain of *Roseomonas mucosa* bacterium comprises a nucleic acid sequence of SEQ ID NO: 1, SEQ ID NO: 2, or SEQ ID NO: 3. Further provide herein are pharmaceutical compositions wherein the at least one strain of *Roseomonas mucosa* comprises a nucleic acid sequence of SEQ ID NO: 1, SEQ ID NO: 2, and SEQ ID NO: 3. Further provide herein are pharmaceutical compositions wherein the at least one strain of *Roseomonas mucosa* comprises isolate RM-A, RM-B or RM-C. Further provide herein are pharmaceutical compositions wherein the at least one strain of *Roseomonas mucosa* is isolate RM-A, RM-B or RM-C. Further provide herein are pharmaceutical compositions wherein the at least one strain of *Roseomonas mucosa* consists of isolates RM-A, RM-B and RM-C.

DETAILED DESCRIPTION

Figures 1A, 1B:
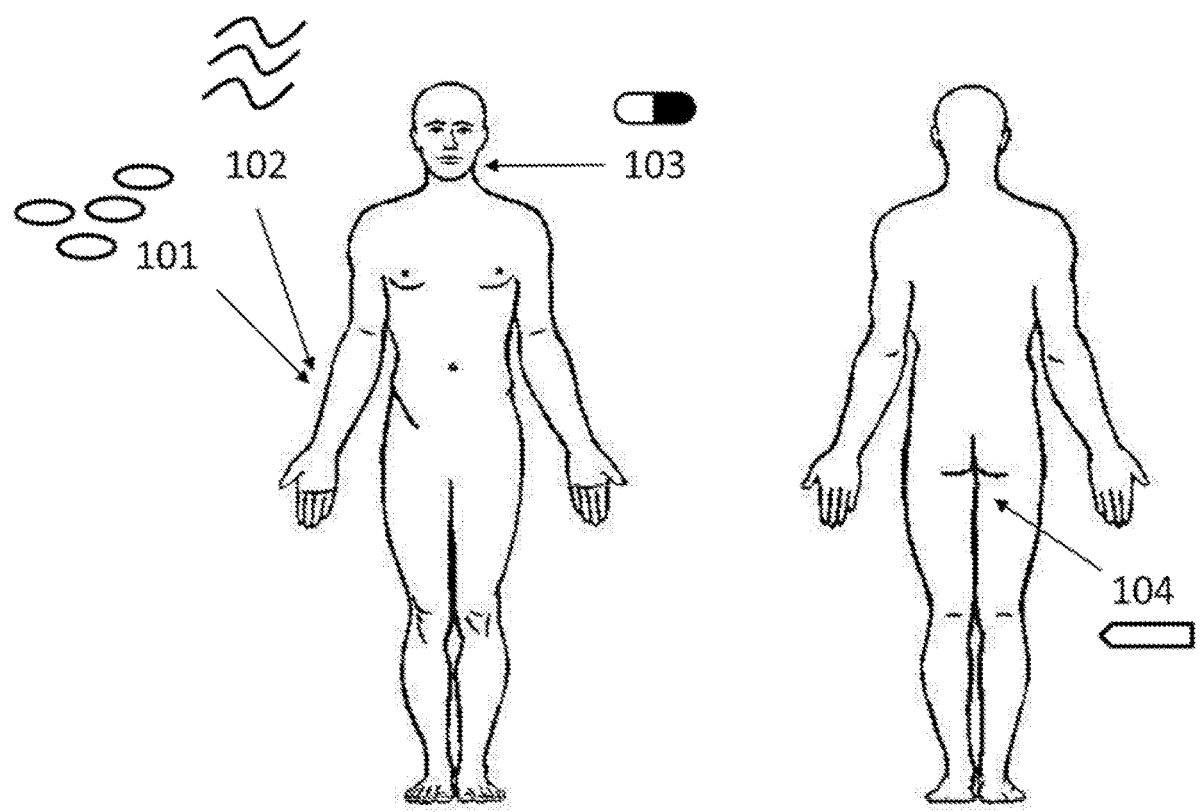
FIG. 1A depicts a route of administration for bacteria via topical administration or oral administration, and for metabolites via topical administration.
FIG. 1B depicts a route of administration for bacteria via rectal administration.

Provided herein are compositions and methods for treatment of a condition associated with skin dysbiosis by administering a metabolite produced by bacteria from a subject that does not have the condition associated with skin dysbiosis. The compositions and methods may further include an additional therapeutic agent for treatment of the condition associated with skin dysbiosis, where the presence of the metabolite enhances the therapeutic effect of the additional therapeutic agent. Described herein are (1) microorganisms for treatment of skin conditions associated with dysbiosis; (2) metabolites for treatment of skin conditions associated with dysbiosis; (3) combination therapies; (4) therapeutic applications; (5) dosage forms; and (6) administration schedules.

Provided herein are pharmaceutical compositions comprising: a metabolite which is more highly produced by bacteria from a subject that does not have the condition associated with skin dysbiosis as compared to production of the metabolite by bacteria from a subject that has the condition associated with skin dysbiosis; a mixture of live bacteria, wherein the mixture comprises: at least one strain of gram negative bacteria derived from a first donor that does not have a skin condition associated with dysbiosis; and, optionally, at least one strain of gram positive bacteria derived from a second donor that does not have the skin condition associated with dysbiosis, wherein the at least one strain of gram negative bacteria and, optionally, the at least one strain of gram positive bacteria are present in an amount sufficient for treatment of the skin condition associated with dysbiosis in a subject in need thereof, and wherein the pharmaceutical composition is in a topical dosage form. Further provided herein are compositions wherein the pharmaceutical composition further comprises a pharmaceutically acceptable carrier. Further provided herein are compositions wherein the skin condition associated with dysbiosis is eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, or acne. Further provided herein are compositions wherein the at least one strain of gram negative bacteria is of the genus *Pseudomonas, Pantoea, Moraxella, Roseomonas*, or *Vitreoscilla*. Further provided herein are compositions wherein the at least one strain of gram negative bacteria is *Roseomonas mucosa, Pseudomonas aeruginosa*, or *Moraxella osloensis*. Further provided herein are compositions wherein the at least one strain of gram negative bacteria is of the genus Staphylococci, Streptococci, Enterococci, Corynebacteriae, or Propionibacterii. Further provided herein are compositions wherein the at least one strain of gram positive bacteria is *Staphylococcus epidermis, Staphylococcus cohnii,* or *Staphylococcus hominis*. Provided herein are methods for treatment of a skin condition associated with dysbiosis, comprising administering the pharmaceutical composition described herein to a subject in need thereof for treatment of the skin condition associated with dysbiosis. Further provided herein are methods wherein the skin condition associated with dysbiosis is eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, or acne. Further provided herein are methods wherein the pharmaceutical composition is administered topically. Further provided herein are methods wherein the pharmaceutical composition is administered to the subject at least two times per a week. Further provided herein are methods wherein the pharmaceutical composition is administered to the subject every other day over a week. Further provided herein are methods wherein the pharmaceutical composition is administered to the subject once a day. Further provided herein are methods wherein the subject is an adult. Further provided herein are methods wherein the subject is a child. Further provided herein are methods wherein the subject is an infant.

Provided herein are methods for treatment of a skin condition associated with dysbiosis, comprising: providing a metabolite produced by bacteria from a subject that does not have the condition associated with skin dysbiosis and at least one species of gram negative bacteria derived from a donor that does not have a skin condition associated with dysbiosis; and topically administering the at least one species of gram negative bacteria to a subject in need thereof, wherein the at least one species of gram negative bacteria is present in an amount sufficient for treatment of a skin condition associated with dysbiosis, wherein the skin condition associated with dysbiosis is eczema, allergic eczema, flexural eczema, infantile eczema, nummular eczema, discoid lupus, prurigo Besnier, psoriasis, vitiligo, rosacea, or acne. Further provided herein are methods wherein the at least one species of gram negative bacteria provides for a relative increase in mRNA levels of defensin β4A, CYP27b1, vitamin D receptor, cathelicidin, or filaggrin in cultured human foreskin-derived primary keratinocytes within 24 hours following infection as compared to a same species type of gram negative bacteria from a subject having the skin condition associated with dysbiosis. Further provided herein are methods wherein the at least one species of gram negative bacteria provides for a relative increase reduction of *Staphylococcus aureus* growth within 24 hours after co-infection in a mouse ear of the at least one species of gram negative bacteria with the a same species type of gram negative bacteria from a subject having the skin condition associated with dysbiosis. Further provided herein are methods wherein the at least one species of gram negative bacteria provides for a relative increase in lysophosphatidylcholine within 24 hours after co-infection in a mouse ear of the at least one species of gram negative bacteria with a same species type of gram negative bacteria from a subject having the skin condition associated with dysbiosis. Further provided herein are methods wherein the at least one species of gram negative bacteria comprises at least 2, 3, 4 or 5 different strains of gram negative bacteria. Further provided herein are methods further comprising administering at least at least one strain of gram positive bacteria derived from a donor that does not have the skin condition associated with dysbiosis. In some instances, the combination of therapeutic agents provides for a therapeutic effect that is enhanced compared to administration of any one agent in the mixture alone. In some instances, a strain of gram positive bacteria is selected based on an increase relative abundance compared the same species of bacteria in a subject suffering from a skin condition associated with dysbiosis. In some instances, the gram positive bacterial species is one or more species in the genus of Staphylococci, Streptococci, Enterococci, Corynebacteriae, or Propionibacterii. In some instances, the Staphylococci species is *Staphylococcus aureus, Staphylococcus hemolyticus, Staphylococcus auricularis, Staphylococcus warneri, Staphylococcus hominis, Staphylococcus epidermidis, Staphylococcus simulans, Staphylococcus sciuri, Staphylococcus capitis, Staphylococcus saprophyticus, Staphylococcus xylosis, Staphylococcus cohnii,* or *Staphylococcus lentus*. In some instances, the Streptococci species is *Streptococcus bovis, Streptococcus agalactae, Streptococcus viridian, Streptococcus pneumonia, Streptococcus salivarius,* or *Streptococcus acidominimus*. In some instances, the Enterococci species is *Enterococcus faecalis, Enterococcus Faecium,* or *Enterococcus gallinarium*. In some instances, the Corynebacteriae species is *Corynebacterium xerosis* or *Corynebacterium minutissimum*. In some instances, the *Propionibacterium* species is *Propionibacterium acnes*. In some instances, the gram-negative bacteria are a species of genera *Pseudomonas, Pantoea, Moraxella, Roseomonas, Vitreoscilla,* or *Methylobacteria*. In some instances the *Roseomonas* genus bacterium is *Roseomonas aerilata, Roseomonas aerophila, Roseomonas aestuarii, Roseomonas alkaliterrae, Roseomonas aquatic, Roseomonas cervicalis, Roseomonas fauriae, Roseomonas frigidaquae, Roseomonas gilardii, Roseomonas lacus, Roseomonas ludipueritiae, Roseomonas mucosa, Roseomonas pecuniae, Roseomonas rhizosphaerae, Roseomonas riguiloci, Roseomonas rosea, Roseomonas soli, Roseomonas stagni, Roseomonas terrae,* or *Roseomonas vinacea*. In some instances the *Pseudomonas* genus bacterium is *Pseudomonas aeruginosa, Pseudomonas luteola,* or *Pseudomonas oryzihabitans*. In some instances the *Pantoea* genus bacterium is *Pantoea septica*. In some instances the *Moraxella* genus bacterium is *Moraxella osloensis*. In some instances the *Vitreoscilla* genus bacterium is *Vitreoscilla filiformis, Vitreoscilla beggiatoides,* or *Vitreoscilla beggiatoides*.

Provided herein is are methods for treatment of a skin condition associated with dysbiosis, comprising: providing a metabolite which is more highly produced by bacteria from a subject that does not have the condition associated with skin dysbiosis as compared to production of the metabolite by bacteria from a subject that has the condition associated with skin dysbiosis and at least one species of gram negative bacteria derived from a first donor that does not have dermatitis; providing at least one species of gram positive bacteria derived from a second donor that does not have dermatitis; and topically administering the at least one species of gram negative bacteria and the at least one species of gram positive bacteria to a subject in need thereof, wherein the at least one species of gram negative bacteria and the at least one species of gram positive bacteria are present in an amount sufficient for treatment of a skin condition associated with dysbiosis, wherein the skin condition associated with dysbiosis is dermatitis. Further provided herein are methods wherein the dermatitis is atopic dermatitis, perioral dermatitis, neurodermatitis, or seborrheic dermatitis. Further provided herein are methods wherein the at least one species of gram negative bacteria provides for a relative increase in mRNA levels of defensin β4A, CYP27b1, vitamin D receptor, cathelicidin, or filaggrin in cultured human foreskin-derived primary keratinocytes within 24 hours following infection as compared to a same species type of gram negative bacteria from a subject having the skin condition associated with dysbiosis. Further provided herein are methods wherein the at least one species of gram negative bacteria provides for a relative increase reduction of *Staphylococcus aureus* growth within 24 hours after co-infection in a mouse ear of the at least one species of gram negative bacteria with the a same species type of gram negative bacteria from a subject having the skin condition associated with dysbiosis. Further provided herein are methods wherein the at least one species of gram negative bacteria provides for a relative increase in lysophosphatidylcholine within 24 hours after co-infection in a mouse ear of the at least one species of gram negative bacteria with a same species type of gram negative bacteria from a subject having the skin condition associated with dysbiosis. Further provided herein are methods wherein the at least one species of gram negative bacteria comprises at least 2, 3, 4 or 5 different strains of gram negative bacteria. In some instances, the combination of therapeutic agents provides for a therapeutic effect that is enhanced compared to administration of any one agent in the mixture alone. In some instances, a strain of gram positive bacteria is selected based on an increase relative abundance compared the same species of bacteria in a subject suffering from a skin condition associated with dysbiosis. In some instances, the gram positive bacterial species is one or more species in the genus of Staphylococci, Streptococci, Enterococci, Corynebacteriae, or Propionibacterii. In some instances, the Staphylococci species is *Staphylococcus aureus, Staphylococcus hemolyticus, Staphylococcus auricularis, Staphylococcus warneri, Staphylococcus hominis, Staphylococcus epidermidis, Staphylococcus simulans, Staphylococcus sciuri, Staphylococcus capitis, Staphylococcus saprophyticus, Staphylococcus xylosis, Staphylococcus cohnii,* or *Staphylococcus lentus*. In some instances, the Streptococci species is *Streptococcus bovis, Streptococcus agalactae, Streptococcus viridian, Streptococcus pneumonia, Streptococcus salivarius,* or *Streptococcus acidominimus*. In some instances, the Enterococci species is *Enterococcus faecalis, Enterococcus Faecium,* or *Enterococcus gallinarium*. In some instances, the Corynebacteriae species is *Corynebacterium xerosis* or *Corynebacterium minutissimum*. In some instances, the *Propionibacterium* species is *Propionibacterium acnes*. In some instances, the gram-negative bacteria are a species of genera *Pseudomonas, Pantoea, Moraxella, Roseomonas, Vitreoscilla,* or *Methylobacteria*. In some instances the *Roseomonas* genus bacterium is *Roseomonas aerilata, Roseomonas aerophila, Roseomonas aestuarii, Roseomonas alkaliterrae, Roseomonas aquatic, Roseomonas cervicalis, Roseomonas fauriae, Roseomonas frigidaquae, Roseomonas gilardii, Roseomonas lacus, Roseomonas ludipueritiae, Roseomonas mucosa, Roseomonas pecuniae, Roseomonas rhizosphaerae, Roseomonas riguiloci, Roseomonas rosea, Roseomonas soli, Roseomonas stagni, Roseomonas terrae,* or *Roseomonas vinacea*. In some instances the *Pseudomonas* genus bacterium is *Pseudomonas aeruginosa, Pseudomonas luteola,* or *Pseudomonas oryzihabitans*. In some instances the *Pantoea* genus bacterium is *Pantoea septica*. In some instances the *Moraxella* genus bacterium is *Moraxella osloensis*. In some instances the *Vitreoscilla* genus bacterium is *Vitreoscilla filiformis, Vitreoscilla beggiatoides,* or *Vitreoscilla beggiatoides*.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included, unless the context clearly dictates otherwise.

The terminology used herein is for the purpose of describing particular instances only and is not intended to be limiting of any embodiment. As used herein, the singular forms "a," "an" and "the" are intended to include the plural forms as well, unless the context clearly indicates otherwise. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Microorganisms for Treatment of Skin Conditions Associated with Dysbiosis

Provided herein are compositions for use in treatment of a skin condition associated with dysbiosis. Such compositions may include isolated and/or purified bacteria and combinations of bacteria from intact human skin, or propagated from such bacteria. These bacteria can function as a healthy microbiota or promote growth of resident microbiome when administered to a subject with a skin condition associated with dysbiosis. The compositions provided may treat, alleviate, delay, or reduce the likelihood of the symptoms of the condition associated with dysbiosis. Exemplary skin conditions associated with dysbiosis for treatment using compositions described herein include, without limitation, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, and acne.

Provided herein are compositions comprising bacteria isolated from a donor subject that does not have a skin condition associated with dysbiosis, e.g., atopic dermatitis. A subject that does not have skin condition associated with dysbiosis is a subject without any observed pathological skin condition. Moreover, the donor subject may not have any pathological condition, for example, a pathological condition of the skin and/or any internal organ. The donor subject can be immunocompetent. The bacteria may be isolated from the skin of the donor subject directly, or propagated in vitro using techniques for culturing bacteria.

Provided herein are genera, species, strains, and combinations of strains or species, originally found within the human skin microbiota of a donor subject without a skin disease associated with dysbiosis. Such species/strains may be selected for their ability to significantly reduce the rate of skin pathogen replication. These species/strains provide a safe and effective means for modulating growth, replication, and disease severity of bacterial pathogens. Moreover, the compositions provided herein exclude pathogenic bacteria. As such, bacteria described herein for use in compositions may be non-pathogenic when administered to the skin of the subject, for example, an immunocompetent subject. Where the bacteria do not cause infection when administered to intact human skin, no pathogenesis is expected to be observed following treatment. Bacteria obtained from a donor subject may be isolated from the skin of various parts of the donor subject's body, for example, the forearm, antecubital fossa, and neck.

Compositions described herein, when administered to a subject having a skin condition associated with dysbiosis, reduce the growth rate of a specific pathogen present in the subject, for example, *S. aureus*. Bacteria with the capacity to durably reduce *S. aureus* in the skin can be identified using a methodology for estimating an Ecological Control Factor (ECF) for constituents within the human microbiota. The ECF can be determined by assessing the antagonistic activity of a given commensal strain or combination of strains towards a given pathogen using an in vitro assay, resulting in observed levels of ecological control at various concentrations of the added commensal strains. The ECF for a commensal strain or combination of strains is similar to the minimal inhibitory concentration (MIC) assessment that is employed in the assessment of antibiotics. The ECF can be used to assess and rank the relative potencies of commensal strains and combinations of strains by the ability to antagonize skin pathogens. The ECF of a commensal strain or combination of 20 strains can be calculated by assessing the concentration of that composition that can mediate a given percentage of inhibition (e.g., at least 10%, at least 20%, at least 50%, at least 70%, at least 75%, at least 80%, at least 85%, at least 90%, at least 95%, or at least 100%) of a target pathogen in an in vitro assay.

Bacteria compositions provided herein may stimulate human keratinocytes. Such stimulation may occur in vivo and/or in vitro. Bacteria can stimulate keratinocytes by increasing the transcription of the mRNA of immune mediators or molecules involved in epithelial barrier function including, for example, increasing production of an mRNA-encoding IL-1β, an mRNA-encoding defensin beta 4, an mRNA-encoding Cyp27b1, an mRNA-encoding a vitamin D receptor, an mRNA-encoding occludin, an mRNA-encoding claudin 1, and/or an mRNA-encoding filaggrin. Bacterial compositions described herein may induce cytokine expression from human cells. Exemplary impacted human cells include, without limitation, the cells of the skin, such as fibroblasts and keratinocytes. Exemplary induced cytokines include, without limitation, an interleukin (IL), such as IL-6 and IL-1β.

In some embodiments, bacteria from only a single genus are included in a composition for treatment of a skin condition associated with dysbiosis. In alternative embodiments, combinations of genera are included in a composition for treatment of a skin condition associated with dysbiosis. In further embodiments, the composition comprises bacteria that are viable. Compositions described herein may include, for example, 1, 2, 3, 4, or 5 genera of bacteria.

Bacteria described herein for treatment of a skin condition associated with dysbiosis may be gram-positive bacteria or gram-negative bacteria. Exemplary gram-positive bacteria include a *Staphylococcus* species including, without limitation, *Staphylococcus epidermis*, *Staphylococcus cohnii*, and *Staphylococcus hominis*. Exemplary gram-negative bacteria include, without limitation, Proteobacteria, Acetobacteraceae, Spirochaetaceae, Enterobacteriales, *Fusobacterium polymorphum*, and Selenomonadales. Exemplary genera of gram-negative bacteria additionally include *Pseudomonas*, *Pantoea*, *Moraxella*, *Roseomonas*, *Vitreoscilla*, and *Methylobacteria* spp. The gram-negative bacteria may be diplococci, coccobacilli, cocci, or bacilli. Additional bacteria for treatment of a skin condition associated with dysbiosis include, without limitation, *Lactobacillus casei* var. *rhamnosus*, *Bifidobacterium animalis* subsp *lactis*. *Bifidobacterium longum*, *Lactobacillus plantarum*, and *Lactobacillus johnsonii*.

In some embodiments, a composition provided herein comprises a viable species of *Roseomonas*. In some embodiments, a composition provided herein comprises a viable species of *Pseudomonas*. In some embodiments, a composition provided herein comprises a viable species of *Roseomonas* and viable species of *Pseudomonas*.

Compositions described herein may include one or more of a species of the *Roseomonas* genus for treatment of a skin condition associated with dysbiosis. Exemplary species of the *Roseomonas* genus include, without limitation, *Roseomonas aerilata*, *Roseomonas aerophila*, *Roseomonas aestuarii*, *Roseomonas alkaliterrae*, *Roseomonas aquatic*, *Roseomonas cervicalis*, *Roseomonas fauriae*, *Roseomonas frigidaquae*, *Roseomonas gilardii*, *Roseomonas lacus*, *Roseomonas ludipueritiae*, *Roseomonas mucosa*, *Roseomonas pecuniae*, *Roseomonas rhizosphaerae*, *Roseomonas riguiloci*, *Roseomonas rosea*, *Roseomonas soli*, *Roseomonas stagni*, *Roseomonas terrae*, and *Roseomonas vinacea*. In some instances, the *Roseomonas mucosa* is, or is derived from, ATCC BAA-692 strain. The bacteria may be viable. The bacteria may be isolated and/or purified. The bacteria may be isolated from a subject not having the skin condition associated with the dysbiosis which is sought to be treated.

Compositions described herein may include one or more of a species of the *Pseudomonas* genus for treatment of a skin condition associated with dysbiosis. Exemplary species of the *Pseudomonas* genus include, without limitation, *Pseudomonas aeruginosa*, *Pseudomonas luteola*, and *Pseudomonas oryzihabitans*. The bacteria may be viable. The bacteria may be isolated and/or purified. The bacteria may be isolated from a subject not having the skin condition associated with dysbiosis which is sought to be treated.

Compositions described herein may include one or more of a species of the *Pantoea* genus for treatment of a skin condition associated with dysbiosis. Exemplary species of the *Pantoea* genus include, without limitation, *Pantoea septica*. The bacteria may be viable. The bacteria may be isolated and/or purified. The bacteria may be isolated from a subject not having the skin condition associated with dysbiosis which is sought to be treated.

Compositions described herein may include one or more of a species of the *Moraxella* genus for treatment of a skin condition associated with dysbiosis. Exemplary species of the *Moraxella* genus include, without limitation, *Moraxella osloensis*. The bacteria may be viable. The bacteria may be isolated and/or purified. The bacteria may be isolated from a subject not having the skin condition associated with dysbiosis which is sought to be treated.

Compositions described herein may include one or more of a species of the *Vitreoscilla* genus for treatment of a skin condition associated with dysbiosis. Exemplary species of the *Vitreoscilla* genus include, without limitation, *Vitreoscilla filiformis*, *Vitreoscilla beggiatoides*, and *Vitreoscilla beggiatoides*. The bacteria may be viable. The bacteria may be isolated and/or purified. The bacteria may be isolated from a subject not having the skin condition associated with dysbiosis which is sought to be treated.

Bacteria of a single species or a single strain can be included in compositions disclosed herein. Combinations of species bacteria can be included in compositions for use in disclosed methods. Thus, a composition described herein can include 1, 2, 3, 4, or 5 species of bacteria. In some embodiments, a composition provided herein includes multiple viable *Roseomonas mucosa* strains from one or more subjects not having a skin condition associated with dysbiosis. In some embodiments, a composition provided herein includes multiple viable *Pseudomonas aeruginosa* strains from one or more donor subjects not having a skin condition associated with dysbiosis. In some embodiments, a composition provided herein includes a viable strain of *Roseomonas mucosa* and a viable strain of *Pseudomonas aeruginosa* one or more donor subjects not having a skin condition associated with dysbiosis. Exemplary skin conditions associated with dysbiosis include, without limitation, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, and acne Compositions provided herein for treatment of a condition associated with skin dysbiosis may include one or more types of bacteria. A composition provided herein may comprise 1 to 15, 2 to 12, 2 to 10, or 2 to 5 different species of bacteria. A composition provided herein may comprise 1 to 15, 2 to 12, 2 to 10, or 2 to 5 different strains of bacteria. A composition provided herein may comprise 1 to 15, 2 to 12, 2 to 10, or 2 to 5 different strains of the same species of bacteria. The composition provided herein may comprise 1, 2, 3, 4 or 5 different strains of the same species of bacteria. The composition provided herein may comprise 1, 2, 3, 4, 5, 6, 7, 8, 9, 10 or more different species of bacteria. In some instances, a composition provided herein can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, or greater than 50 types of bacteria, as defined by genus, species, or operational taxonomic unit (OTU). Strains described herein may be gram negative or gram positive. Such strains may be derived from a donor that does not have a certain dysbiosis of the skin for which the strain is to be used to treat.

Bacteria described herein may be transformed with a heterologous nucleic acid, such as in the form of a plasmid. For example, the plasmid may comprise an expression vector encoding for protein of interest. Such a mechanism provides a means for introduction of exogenous DNA can be introduced bacterial cells with standard techniques, such as electroporation or calcium phosphate-mediated transfection.

In some embodiments, the heterologous nucleic acid is included in a plasmid. A plasmid generally contains multiple genetic elements positionally and sequentially oriented with other necessary genetic elements, such that the nucleic acid in a nucleic acid cassette can be transcribed and when necessary translated in the transfected cells. Plasmids can include nucleic acids that are derived from DNA via a plasmid vector, cosmids, or phagemids, where one or more heterologous nucleic acid can be inserted. The heterologous nucleic acid can encode a protein of interest, which can be operably-linked to a promoter for expression of the bacteria.

Plasmids generally contain one or more unique restriction sites. In addition, a plasmid can confer well-defined phenotypes on the host organism, which can be selectable or readily-detected, for example, drug resistance. Thus, the plasmid can include an expression cassette, where a polypeptide is encoded. Expression can include the efficient transcription of an inserted gene, nucleic acid sequence, or nucleic acid cassette with the plasmid.

In some embodiments, when a circular plasmid is transferred into a bacterial cell, the plasmid can be an autonomously replicating, extra-chromosomal DNA molecule, distinct from the normal bacterial genome and non-essential for bacterial cell survival under non-selective conditions. Persistent expression can refer to introduction of genes into the cell together with genetic elements which enable episomal (extra-chromosomal) replication and/or maintenance of the genetic material in the cell. Persistent expression can lead to apparently stable transformation of the cell without the integration of the novel genetic material into the chromosome of the host cell. A plasmid can also introduce genetic material into chromosomes of the targeted cell. Gene expression after stable introduction can permanently alter the characteristics of the cell and cell progeny by replication leading to stable transformation.

Heterologous nucleic acids described herein may provide for increased production of a metabolite that is increased in production from bacteria of skin from a healthy donor subject in comparison to a similar strain of the bacteria from a subject having a skin condition associated with dysbiosis. Heterologous nucleic acids described herein may provide for decreased production of a metabolite that is decreased in production from bacteria of skin from a healthy donor subject in comparison to a similar strain of the bacteria from a subject having a skin condition associated with dysbiosis. Mechanisms for decreasing production may include, without limitation, gene silencing or knockdown, e.g., siRNA, shRNA, RNAi, or CRISPR/Cas mechanisms.

Methods for producing bacterial strains for incorporation in a composition described herein optionally include processing steps of organism banking, organism production, and preservation. For organism banking, strains of bacteria can be isolated directly from a specimen, for example, from human skin or a banked stock. Bacteria can be cultured on a nutrient agar or broth that supports growth to generate viable biomass. The cultured biomass can be preserved in multiple aliquots for long-term storage. Bacteria may be isolated directly from the skin of a human donor subject. Generally, the human donor subject does not have a skin condition associated with dysbiosis, e.g., atopic dermatitis, or any other skin condition. Bacteria can also be isolated from other sources including, for example, commercial sources or environmental samples.

Microbial Metabolites

Certain strains or species of bacteria have been reported to have a therapeutic effect on skin conditions associated with dysbiosis. The therapeutic effect of such bacteria may be attributed to the metabolic profile of the bacteria, i.e. metabolite produced by the bacteria. In some instances, bacteria can produce lipids that have a beneficial effect on restoring barrier function and regulating immune response.

Provided herein are compositions and methods for therapy for treatment of a skin condition associated with dysbiosis by administration of one or more metabolites which alleviates the condition. The one or more metabolites which alleviate the skin condition associated with dysbiosis may be those which are increased in production from a species of bacteria present on the skin of an individual without the skin condition as compared to the species of bacteria from an individual having the skin condition. The one or more metabolites may be part of a combination therapy also including a species of bacteria obtained or derived from a donor subject that does not have the skin condition associated with dysbiosis. For example, the metabolite can be obtained from a species of bacteria obtained or derived from donor subject that does not have the skin condition associated with dysbiosis. Metabolites described herein for treatment of a skin disease associated with dysbiosis for use in a composition described herein include, without limitation, those listed in Table 1. Provided herein are methods for treatment of a skin condition associated with dysbiosis comprising administering to a subject in need thereof a composition comprising metabolites listed in Table 1, optionally in addition to administration of one or more species of bacteria described herein for treatment of the skin condition. When metabolite administration is part of a co-therapy, the metabolite can enhance the therapeutic effect of the one or more bacteria administered. Exemplary skin conditions associated with dysbiosis include, without limitation, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, and acne.

TABLE 1

Metabolites

| Category | Metabolite |
|---|---|
| Lipids | Phosphatidylethanolamine |
| | Phosphatidylethanolamine 36:2 |
| | Phosphatidylethanolamine 14:0/20:1 |
| | Phosphatidylethanolamine 22:1/14:1 |
| | Phosphatidylethanolamine 36:2 |
| | Phosphatidylcholine |
| | Phosphatidylcholine 37:0 |
| | Phosphatidylcholine 37:2 |
| | Phosphatidylcholine 38:2 |
| | Phosphatidylcholine(18:2(9Z,12Z)/18:0) |
| | Lysophosphatidylcholine |
| | 8-keto palmitic acid |
| Peptide | Tyr-Leu-Arg |
| Sugar | maltopentaose |
| Nucleic acid, nucleoside, or nucleotide | 2'-deoxyguanosine 5'-monophosphate |

TABLE 1-continued

Metabolites

| Category | Metabolite |
|---|---|
| Additional metabolites | N4-acetylaminobutanal |
| | 5-ethylpentadecane-2,4-dione |
| | Ricinoleic acid methyl ester |
| | Trenbolone acetate |
| | N-(2-hydroxyethyl)-11(12)-epoxy-5Z,8Z,14Z-eicosatrienamide |

Combination Therapies

Provided herein are combination therapies for treatment of a skin condition associated with dysbiosis. In a first design, the combination therapy includes administration of a first therapeutic agent, wherein the first therapeutic agent comprises one or more metabolites, and a second therapeutic agent for treatment of the skin condition, wherein the combination of administering the therapeutic agents provides for an enhanced therapeutic effect than administration of either agent alone. In further instances, the first therapeutic agent is present in an amount to increase the therapeutic effect of the second therapeutic agent. In some instances, one or more metabolites enhance the therapeutic effect of a second therapeutic agent. Exemplary metabolites are described herein, including those listed in Table 1. The combination therapy may further include administration of a third therapeutic agent for treatment of the skin condition. Exemplary therapeutic agents for inclusion are listed in Table 2. In a second design, the combination therapy includes administration of a first therapeutic agent, wherein the first therapeutic agent comprises a species or strain of bacteria described herein for treatment of a skin condition associated with dysbiosis, and a second therapeutic agent for treatment of the skin condition, where the second therapeutic agent is listed in Table 2, and wherein the combination of therapeutic agents provides for an enhanced therapeutic effect than administration of either agent alone. In further instances, the first therapeutic agent is present in an amount to increase the therapeutic effect of the second therapeutic agent, or vice versa. In some embodiments, the combination therapy further includes a mixture of live bacteria, wherein the mixture comprises: at least one strain of gram negative bacteria derived from a donor that does not have skin dysbiosis; and at least one strain of gram positive bacteria derived from a second donor that does not have skin dysbiosis, wherein the at least one strain of gram negative bacteria and the at least one strain of gram positive bacteria are present in an amount sufficient for treatment of skin dysbiosis in a subject in need thereof.

Provided herein are compositions for treatment of a skin condition associated with dysbiosis, comprising a metabolite, wherein the metabolite is present in an amount sufficient to reduce atopic dermatitis in a subject in need thereof, and wherein the metabolite is produced from a species of gram-negative bacteria that is more highly abundant in skin from a subject that does not have atopic dermatitis as compared to abundance of the species in skin from a subject having atopic dermatitis; a first agent that is a gram positive bacterial strain; and a second agent that is a gram negative bacterial strain.

Combination therapies described herein may include donor derived bacterial strains, where the donor does not show signs of a skin condition associated with dysbiosis. In some instances, compositions for combination therapy described herein comprise a plurality of strains for each species included in the composition. In some instances, the combination of therapeutic agents provides for a therapeutic effect that is enhanced compared to administration of any one agent in the mixture alone. In some instances, a strain of gram positive bacteria is selected based on an increase relative abundance compared the same species of bacteria in a subject suffering from a skin condition associated with dysbiosis. Exemplary gram positive bacterial species for inclusion are, without limitation, one or more species in the genus of Staphylococci, Streptococci, Enterococci, Corynebacteriae, or Propionibacterii. Exemplary Staphylococci species for combination with a gram negative species described herein include, without limitation, *Staphylococcus aureus, Staphylococcus hemolyticus, Staphylococcus auricularis, Staphylococcus warneri, Staphylococcus hominis, Staphylococcus epidermidis, Staphylococcus simulans, Staphylococcus sciuri, Staphylococcus capitis, Staphylococcus saprophyticus, Staphylococcus xylosis, Staphylococcus cohnii*, and *Staphylococcus lentus*. Exemplary Streptococci species for combination with a gram negative species described herein include, without limitation, *Streptococcus bovis, Streptococcus agalactae, Streptococcus viridian, Streptococcus pneumonia, Streptococcus salivarius*, and *Streptococcus acidominimus*. Exemplary Enterococci species combination with a gram negative species described herein include, without limitation, *Enterococcus faecalis, Enterococcus Faecium*, and *Enterococcus gallinarium*. Exemplary Corynebacteriae species for combination with a gram negative species described herein include, without limitation, *Corynebacterium xerosis* and *Corynebacterium minutissimum*. Exemplary *Propionibacterium* species for combination with a gram negative species described herein include, without limitation, *Propionibacterium acnes*. Exemplary gram positive bacteria for combination with a gram negative species described herein include, without limitation, *Staphylococcus epidermidis, Staphylococcus hominis, Staphylococcus cohnii*, or *Propionibacterium acnes*. In some instances, the *Staphylococcus epidermidis* is, or is derived from, ATCC 12228 strain. In some instances, the *Propionibacterium acnes* is, or is derived from, ATCC 6919 strain. Exemplary genera of gram-negative bacteria additionally include *Pseudomonas, Pantoea, Moraxella, Roseomonas, Vitreoscilla*, and *Methylobacteria* spp. Exemplary species of the *Roseomonas* genus include, without limitation, *Roseomonas aerilata, Roseomonas aerophila, Roseomonas aestuarii, Roseomonas alkaliterrae, Roseomonas aquatic, Roseomonas cervicalis, Roseomonas fauriae, Roseomonas frigidaquae, Roseomonas gilardii, Roseomonas lacus, Roseomonas ludipueritiae, Roseomonas mucosa, Roseomonas pecuniae, Roseomonas rhizosphaerae, Roseomonas riguiloci, Roseomonas rosea, Roseomonas soli, Roseomonas stagni, Roseomonas terrae*, and *Roseomonas vinacea*. Exemplary species of the *Pseudomonas* genus include, without limitation, *Pseudomonas aeruginosa, Pseudomonas luteola*, and *Pseudomonas oryzihabitans*. Exemplary species of the *Pantoea* genus include, without limitation, *Pantoea septica*. Exemplary species of the *Moraxella* genus include, without limitation, *Moraxella osloensis*. Exemplary species of the *Vitreoscilla* genus include, without limitation, *Vitreoscilla filiformis, Vitreoscilla beggiatoides*, and *Vitreoscilla beggiatoides*.

Therapeutic agents may be, without limitation, a microorganism, small molecule, antibody, calcineurin inhibitor, immune modulator, or steroid. Examples of such agents are provided, without limitation, in Table 2. Each of the first, second, or third therapeutic agents may be administered simultaneously or sequentially. Each of the first, second, or third therapeutic agents may be administered in similar or different dosage forms (oral, rectal, or topical). Exemplary skin conditions associated with dysbiosis include, without limitation, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, and acne.

TABLE 2

Therapeutic agents.

| Type | Description |
|---|---|
| Microorganism (optionally obtained from or derived from a donor subject not having a skin condition associated with dysbiosis) | *Roseomonas mucosa* |
| | *Pseudomonas aeruginosa* |
| | *Pantoea septica* |
| | *Vitreoscilla filiformis* |
| | *Vitreoscilla beggiatoides* |
| | *Vitreoscilla beggiatoides* |
| | *Moraxella osloensis* |
| | *Lactobacillus casei* var. *rhamnosus* |
| | *Bifidobacterium animalis* subsp *lactis*. |
| | *Bifidobacterium longum* |
| | *Lactobacillus plantarum* |
| | *Lactobacillus johnsonii* |
| | *Staphylococcus epidermis* |
| | *Staphylococcus cohnii* |
| | *Staphylococcus hominis* |
| | *Propionibacterium acnes* |
| Calcineurin inhibitors | Cyclosporine |
| | Pimecrolimus |
| | Tacrolimus |
| | Voclosporin |
| Antibody | Omalizumab |
| | Ligelizumab |
| | Ustekinumab |
| | Lebrikizumab |
| | Tralokinumab |
| | Secukinumab |
| | Nemolizumab |
| | Dupilumab |
| | Mepolizumab |
| | Fezakinumab |
| | GBR 830 |
| | Tezepelumab |
| Immune modulators | Cyclosporine |
| | Methotrexate |
| | Azathioprine |
| | Mycophenolic acid |
| | Mycophenolate mofetil |
| | Thymic stromal lymphopoietin (TSLP) antagonists |
| | OX40 antagonists |
| Small Molecules | Fevipiprant |
| | Timapiprant |
| | Baricitinib |
| | AQX-1125 |
| | Aprimelast |
| | Serlopitant |
| | Tradipitant |
| | Asimadoline |
| | Tofacitinib |
| | Upadacitinib |
| | PF-04965842 |
| Steroid | Corticosteroids |
| | Betamethasone dipropionate |
| | Betamethasone valerate |
| | Desonide |
| | Desoximetasone |
| | Diflorasone diacetate |
| | Fluocinonide |
| | Flurandrenolide |
| | Flurandrenolide |
| | Fluticasone propionate |
| | Fluocinolone acetonide |
| | Hydrocortisone |
| | Amcinonide |
| | Halcinonide |

TABLE 2-continued

Therapeutic agents.

| Type | Description |
|---|---|
| | Triamcinolone |
| | Triamcinolone Acetonide |
| | Mometasone |
| | Alclometasone |

Therapeutic Applications: Skin Conditions Associated with Dysbiosis

Provided herein are methods and compositions for the treatment of skin conditions associated with dysbiosis. Such conditions are often associated with a disruption in the skin barrier and inflammation in regions of the skin. Affected subjects may have a rash, itchiness, redness, swelling, vesicle formation (minute blisters), cracking, weeping, crusting, and scaling of the skin. Compositions and methods described herein for treatment of the skin condition associated with dysbiosis may experience a lessening of the rash, itchiness, redness, swelling, vesicle formation (minute blisters), cracking, weeping, crusting, or scaling of the skin associated with the skin condition. Exemplary skin conditions associated with dysbiosis include, without limitation, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, and acne. Treatments described herein may also provide for treatment of secondary disease conditions associated with the primary disease being treated. For example, in the case of treating atopic dermatitis, a composition described herein also provides for treatment or prevention of asthma, allergies, and allergic rhinitis (hay fever).

Dosage Forms

Compositions and pharmaceutical compositions provided herein may be formulated for topical, oral, or rectal administration. FIG. 1A depicts a route of topical administration for bacteria 101 and metabolites 102, or a route of oral administration for bacteria 103, and FIG. 1B depicts a route of rectal administration for bacteria 104. Exemplary oral dosage forms include, without limitation, a tablet, lozenge, pastille capsule, tab, granules, powder, liquid, emulsion, suspension and syrup. Exemplary rectal dosage forms include, without limitation, a suppository, and enema solution, rectal foam, or rectal gel. Exemplary topical dosage forms include, without limitation, creams, ointments, lotions, and sterile aqueous solutions or suspensions. Compositions can include an aqueous carrier, and be applied as a spray to the skin.

Creams are viscous liquids or semisolid emulsions, either oil-in-water or water-in-oil. Cream bases are water-washable, and contain an oil phase, an emulsifier, and an aqueous phase. The oil or "internal" phase generally contains of petrolatum and a fatty alcohol, such as acetyl or stearyl alcohol. The aqueous phase can exceed the oil phase in volume, and can contain a humectant. The emulsifier in a cream formulation can be a nonionic, anionic, cationic, or amphoteric surfactant.

Lotions can include preparations to be applied to the skin surface without friction. Lotions are typically liquid or semiliquid preparations in which particles are present in a water or alcohol base. Lotions can be suspensions of solids or a liquid oily emulsion of the oil-in-water type. Lotions can be used for treating large body areas, because of the ease of applying a more fluid composition. It is generally necessary that the insoluble matter in a lotion be finely divided. Lotions typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize, or preserve the solute. Common examples of solvents used in preparing topical solutions are ethanol, water, propylene glycol or any other-acceptable vehicles. These can be applied in any manner, such as spraying them on the skin, painting them on the skin, or wetting a bandage with the solution.

Gels are semisolid, suspension-type systems. Single-phase gels contain organic macromolecules distributed substantially uniformly throughout the carrier liquid, which can be aqueous, contain an alcohol, or hydrophobic. Organic macromolecules, including gelling agents, can be cross-linked acrylic acid polymers, e.g., carboxypolyalkylenes (CARBOPOL®). Non-limiting examples of gels include hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methyl cellulose; gums, such as tragacanth and xanthan gum; sodium alginate; and gelatin. To prepare a uniform gel, dispersing agents, such as alcohol or glycerin can be added, or the gelling agent can be dispersed by trituration, mechanical mixing or stirring, or combinations thereof.

Ointments can also be used in the disclosed methods. Ointments are semisolid preparations that are typically based on petrolatum or other petroleum derivatives. The specific ointment base to be used, as will be appreciated by those skilled in the art, is one that will provide for a number of desirable characteristics, e.g., emolliency or the like. An ointment base is generally inert, stable, non-irritating, and non-sensitizing. Ointment bases may be oleaginous bases, emulsifiable bases, emulsion bases, or water-soluble bases.

Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, acetyl alcohol, glyceryl monostearate, lanolin, and stearic acid. Water-soluble ointment bases are prepared from polyethylene glycols of varying molecular weight.

Pastes are semisolid dosage forms in which the active agent is suspended in a suitable base, and are also of use. Depending on the nature of the base, pastes are divided between fatty pastes or those made from single-phase aqueous gels. The base in a fatty paste can be petrolatum or hydrophilic petrolatum or the like. The pastes made from single-phase aqueous gels can incorporate carboxymethylcellulose or the like as a base.

A topical composition can be any form suitable for application to the body surface including, for example, as a cream, lotion, spray, solution, gel, foam, ointment, paste, plaster, paint, bioadhesive, bandage, spray, suspension, and containing liposomes, micelles, and/or microspheres. A topical composition can be used in combination with an occlusive overlayer so that moisture evaporating from the body surface can be maintained within the formulation upon application to the body surface and thereafter. A cream, lotion, gel, ointment, paste, or the like can be spread on the affected surface.

A solution can be applied in the same way, but more typically will be applied with a dropper, swab, sprayer or the like, and carefully applied to the affected areas. Compositions can be applied directly to the target location, for example in a topical preparation, such as an ointment, or as a part of a dressing or a bandage. Compositions can be formulated as a unit dosage, for administration by any device for administration to the skin. The unit dosage can be a reservoir of the active agent in a carrier, for example an adhesive carrier capable of adhering to the skin for a desired period of time, such as at least a day or more.

Pharmaceutical compositions provided herein may include a pharmaceutically-acceptable carrier, and can include additional compounds. In some embodiments, pharmaceutical compositions include additional active and/or inactive materials, which can be in prepared as single dosage unit or in a multi-dose format.

Pharmaceutical compositions described herein may include a carrier that comprises one or more of a buffering agent, a preservative, a stabilizer, a binder, a compaction agent, a lubricant, a dispersion enhancer and/or a coloring agent. Non-limiting examples of suitable buffering agents include sodium citrate, magnesium carbonate, magnesium bicarbonate, calcium carbonate, and calcium bicarbonate. Non-limiting examples of suitable preservatives include antioxidants, such as alpha tocopherol and ascorbate, parabens, chlorobutanol, and phenol. Non-limiting examples of suitable binders include sucrose, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. A pH buffering agent(s) can, if employed and when dissolved in an aqueous component of the composition, provide a pH in the range of 5 to 7 (5 e.g. about pH 5.5).

Pharmaceutical compositions described herein may include a carrier that comprises other ingredients including, for example, ingredients that sustain growth of the bacteria. In some embodiments, pharmaceutical compositions can include a nutrient. In some embodiments, compositions include at least one carbohydrate or saccharide. A carbohydrate can be a monosaccharide, a disaccharide, trisaccharide, oligosaccharide, or polysaccharide. Non-limiting examples of carbohydrates include glucose, sucrose, galactose, mannose, ribose, arabinose, xylose, fructose, maltose, cellobiose, lactose, raffinose, stachyose, starch, glycogen, and cellulose. Carbohydrates can contain modified saccharide unit, including, for example, 2'-deoxyribose in which a hydroxyl group is removed, 2'-fluororibose in which a hydroxyl group is replaced with a fluorine, and or N-acetyl-glucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers.

Pharmaceutical compositions described herein may include a carrier that comprises one or more lipids. A lipid can include fats, oils, triglycerides, cholesterol, phospholipids, and fatty acids. Fats, oils, and fatty acids can be saturated, unsaturated (cis or trans), or partially unsaturated (cis or trans). Non-limiting examples of fatty acids include lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid, α-linolenic acid, and γ-linolenic acid.

Pharmaceutical compositions described herein may include a carrier that comprises at least one supplemental mineral or mineral source. Non-limiting examples of minerals include chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals, such as carbonyl minerals, and reduced minerals, and combinations thereof. In some embodiments, compositions include at least one supplemental vitamin. Supplemental vitamins can be fat-soluble or water-soluble. Non-limiting examples of vitamins include vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

Various other additives can be included in the compositions. Non-limiting examples of additives include antioxidants, astringents, perfumes, preservatives, emollients, pigments, dyes, humectants, propellants, and sunscreen agents, as well as other classes of materials whose presence can be pharmaceutically or otherwise desirable. Non-limiting examples of optional additives include preservatives, such as sorbate; solvents, such as isopropanol and propylene glycol; astringents, such as menthol and ethanol; emollients, such as polyalkylene methyl glucosides; humectants, such as glycerin; emulsifiers, such as glycerol stearate, PEG-100 stearate, polyglyceryl-3 hydroxylauryl ether, and polysorbate 60; sorbitol and other polyhydroxyalcohols, such as polyethylene glycol; sunscreen agents, such as octyl methoxyl cinnamate (Parsol MCX) and butyl methoxy benzoylmethane (Parsol 1789); antioxidants, such as ascorbic acid (vitamin C), α-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants, such as swelling clays and cross-linked carboxypolyalkylenes.

Other additives include materials that condition the skin. Such materials can soften the skin by retarding the decrease of water content of the skin and/or protect the skin. Conditioners and moisturizing agents include, for example, pyrrolidine carboxylic acid and amino acids; organic antimicrobial agents, such as triclosan and benzoic acid. Further additives include anti-inflammatory agents, such as acetylsalicylic acid and glycyrrhetinic acid; anti-seborrhoeic agents, such as retinoic acid; vasodilators, such as nicotinic acid; inhibitors of melanogenesis, such as kojic acid; and mixtures thereof.

In some embodiments, compositions described herein include alpha hydroxyacids, alpha ketoacids, polymeric hydroxyacids, moisturizers, collagen, marine extract, and antioxidants, such as ascorbic acid (vitamin C) and α-tocopherol (Vitamin E). Sunscreens can also be included. Additional, components, such as enzymes, herbs, plant extracts, and glandular or animal extracts can be added to the composition. The amounts of these various additives are those conventionally used in the cosmetics field, and range, for example, from about 0.01% to about 20% of the total weight of the topical formulation.

Compositions described herein can also include antimicrobial agents, to prevent spoilage upon storage, for example, to inhibit growth of microbes, such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Compositions described herein can also contain irritation-mitigating additives to reduce or eliminate the possibility of skin irritation or skin damage resulting from the chemical entity to be administered, or other components of the composition. Suitable irritation-mitigating additives include, for example, α-tocopherol; monoamine oxidase inhibitors, particularly phenyl alcohols, such as 2-phenyl-1-ethanol; glycerin; salicylates; ascorbates; ionophores, such as monensin; amphiphilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt %, more typically not more than about 5 wt %, of the formulation. Non-limiting examples of suitable pharmacologically-active agents that can be incorporated into the present formulations can include the following: agents that improve or eradicate pigmented or non-pigmented age spots, keratoses, and wrinkles; local anesthetics and analgesics; corticosteroids; retinoids; and hormones. Some examples of topical pharmacologically-active agents include acyclovir, amphotericins, chlorhexidine, clotrimazole, ketoconazole, econazole, miconazole, metronidazole, minocycline, phenytoin, para-amino benzoic acid esters, octyl methoxycinnamate, octyl salicylate, oxybenzone, dioxybenzone, tocopherol, tocopheryl acetate, zinc pyrithione, diphenhydramine, pramoxine, lidocaine, procaine, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, tacrolimus, and topical steroids, such as alclometasone, amcinonide, betamethasone, clobetasol, desonide, dexoximetasone, diflorasone, flucinonide, flurandrenolide, halobetasol, halcinonide, hydrocortisone, and/or triamcinolone.

Although topical formulations, such as creams and salves, are formulated for dermal delivery, the delivery systems can include time-release, delayed release, or sustained release delivery systems. Such systems can avoid repeated administrations of the compositions, increasing convenience to the subject and the physician. Non-limiting examples of release delivery systems include (a) erosional systems and (b) diffusional systems in which an active component permeates at a controlled rate from a polymer. The delivery system can include collagen, fibrin, or a membrane extract, such as a basal membrane extract, for example, in which compositions are formulated for administration to the skin. Suitable basement membrane extracts include a biologically active polymerizable extract containing in parts by weight about 60-85% laminin, 5-30% collagen IV, 1-10% nidogen, 1-10% heparan sulfate proteoglycan, and 1-5% entactin. BME can support normal growth and differentiation of various cell types including epithelial cells when cultured. Basal membrane extracts are well known in the art and are commercially available.

Compositions described herein may comprise a single (unit) dose of bacteria. Compositions described herein may comprise $10^3$ to $10^{12}$ colony forming units (cfu) of bacteria or a bacterial strain described herein. Compositions described herein may comprise about $10^3$ to $10^{11}$ cfu, $10^3$ to $10^{10}$ cfu, $10^3$ to $10^9$ cfu, $10^3$ to $10^8$ cfu, $10^3$ to $10^7$ cfu, $10^3$ to $10^6$ cfu, $10^3$ to about $10^5$ cfu, $10^3$ to $10^4$ cfu, $10^4$ to $10^{12}$ cfu, $10^4$ to $10^{11}$ cfu, $10^4$ to $10^{10}$ cfu, $10^4$ to $10^9$ cfu, $10^4$ to $10^8$ cfu, $10^4$ to $10^7$ cfu, $10^4$ to $10^6$ cfu, $10^5$ to $10^{12}$ cfu, $10^5$ to $10^{11}$ cfu, about $10^5$ to about $10^{10}$ cfu, $10^6$ to $10^{12}$ cfu, $10^7$ to $10^{12}$ cfu, $10^8$ to $10^{12}$ cfu, $10^9$ to $10^{12}$ cfu, $10^{10}$ to $10^{12}$ cfu, $10^{11}$ to $10^{12}$ cfu, or $10^6$ to $10^{10}$ cfu of bacteria or a bacterial strain described herein. In some embodiments, compositions comprise about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu of bacteria or a bacterial strain described herein.

In other embodiments, a composition described herein comprises at least about 0.01% by weight, at least about 0.05% by weight, at least about 0.1% by weight, at least about 0.2% by weight, at least about 0.3% by weight, at least about 0.4% by weight, at least about 0.5% by weight, at least about 0.6% by weight, at least about 0.7% by weight, at least about 0.8% by weight, at least about 0.9% by weight, at least about 1.0% by weight, at least about 1.5% by weight, at least about 2.0% by weight, at least about 3.0% by weight, at least about 4.0% by weight, at least about 5.0% by weight, at least about 6.0% by weight, at least about 7.0% by weight, at least about 8.0% by weight, at least about 9.0% by weight, at least about 10.0% by weight, at least about 11.0% by weight, at least about 12.0% by weight, at least about 13.0% by weight, at least about 14.0% by weight, at least about 15.0% by weight, at least about 16.0% by weight, at least about 17.0% by weight, at least about 18.0% by weight, at least about 19.0% by weight, at least about 20.0% by weight, at least about 25.0% by weight, at least about 30.0% by weight, at least about 35.0% by weight, at least about 40.0% by weight, at least about 45.0% by weight, or at least about 50.0% by weight of bacteria or bacterial strain described herein. In some embodiments, compositions can include from 0.01% to 30% by weight, from about 0.01% to 20% by weight, from 0.01% to 5% by weight, from 0.1% to 30% by weight, from 0.1% to 20% by weight, from 0.1% to about 15% by weight, from 0.1% to 10% by weight, from 0.1% to 5% by weight, from 0.2% to 5% by weight, from 0.3% to 5% by weight, from 0.4% to 5% by weight, from 0.5% to 5% by weight, or from 1% to 5% by weight of bacteria or bacterial strain described herein.

Administration

Subjects having a skin condition associated with dysbiosis may be treated using compositions described herein. The subject can be a human. In some embodiments, the subject is a child. The subject can be 12, 11, 10, 9, 8, 7, 6, 5, 4, 3, 2, or 1 year(s) of age. In some embodiments, the subject is an adolescent. The subject can be 12, 13, 14, 15, 16, 17, or 18 years of age. The subject is an infant or less than 1 year of age. In other embodiments, the subject is an adult. The subject can be about 20 years of age, about 25 years of age, about 30 years of age, about 35 years of age, about 40 years of age, about 45 years of age, about 50 years of age, about 55 years of age, about 60 years of age, about 65 years of age, about 70 years of age, about 75 years of age, about 80 years of age, or more than 80 years of age. The subject can be immunocompromised or can have an intact immune system (immunocompetent).

Compositions can be applied to the skin, such as at lesion areas and round lesion area, or at areas of intact skin (non-lesion areas) to prevent lesions for forming. Compositions can be used to reduce lesion size. Compositions can be applied at one time (daily) or at multiple times throughout the day. In some embodiments, compositions can be applied 2 times, 3 times, 4 times, or 5 times per day. In some embodiments, compositions can be applied every other day, daily over a week, every other day over a week, every week, 2 times per week, 3 times per week, 4 times per week, 5 times per week, 6 times per week, or 7 times per week. Compositions can be formulated as a unit dose for administration.

For treatment of the skin, a therapeutically-effective amount of a composition can be locally administered to the affected area. Affected areas can include, for example, the antecubital fossa, neck, and forearm. Pharmacological compositions disclosed herein facilitate the use of at least one species of bacteria for the treatment of atopic dermatitis. Such compositions can be suitable for delivery of the active ingredient to any suitable subject, such as, but not limited to, a human subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (physiologically or pharmaceutically) acceptable carriers, as well as optional auxiliaries that facilitate processing of the active compounds into preparations which can be used pharmaceutically, as discussed above.

Compositions and methods described herein may be used for the treatment of a skin condition associated with dysbiosis. Treatment of the skin condition associated with dysbiosis may result in reduced lesion size, reduced number of lesions, and/or a reduction in related symptoms. In addition, treatment of the skin condition associated with dysbiosis with a composition or method described herein may reduce $S.$ $aureus$ in the skin of a subject in need thereof. Compositions and methods described herein may provide for enhanced barrier function of the skin as measured by trans-epidermal water loss. Administrations described herein, e.g., topical, oral, or rectal, may reduce reoccurrences, so that additional incidents of the skin condition associated with dysbiosis are reduced in number, intensity, or frequency. The administration may increase the time of remission, such as the length of time between incidents. In some embodiments, an additional incident of skin condition associated with dysbiosis does not occur for 1, 2, 3, 4, 5, 6, 7, 8, 9, 10, 11, or 12 weeks following application. In some embodiments, an additional incident skin condition associated with dysbiosis does not occur for 1, 2, 3, 4, 5, 6, 7, 8, 9, 10, 11, or 12 months following the topical application. Exemplary skin conditions associated with dysbiosis include, without limitation, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, and acne.

Compositions and methods described herein may be used for the treatment of atopic dermatitis. Treatment of the atopic dermatitis may result in reduced lesion size, reduced number of lesions, and/or a reduction in related symptoms. In addition, treatment of atopic dermatitis with a composition or method described herein may reduce $S.$ $aureus$ in the skin of a subject in need thereof. Compositions and methods described herein may provide for enhanced barrier function of the skin as measured by trans-epidermal water loss. Atopic dermatitis can occur as flare-ups, and there can be periods of remission. Administrations described herein, e.g., topical, oral, or rectal, may reduce reoccurrences, so that additional incidents of atopic dermatitis are reduced in number, intensity, or frequency. The administration may increase the time of remission, such as the length of time between incidents. In some embodiments, an additional incident of atopic dermatitis does not occur for 1, 2, 3, 4, 5, 6, 7, 8, 9, 10, 11, or 12 weeks following application. In some embodiments, an additional incident of atopic dermatitis does not occur for 1, 2, 3, 4, 5, 6, 7, 8, 9, 10, 11, or 12 months following the topical application.

Methods provided herein for treatment of a skin condition associated with dysbiosis may include measuring the microbiota of the skin of the subject. Specifically, diagnostic assays can be performed to determine whether the bacterial flora in the skin of a subject is altered following treatment compared to an original assessment. Alteration of bacterial phyla, bacterial classes, bacterial orders, bacterial families, bacterial genera, and/or bacterial species in the skin of a subject with atopic dermatitis can be determined. In some embodiments, the amount of $S.$ $aureus$ modified in the skin of the subject following treatment can be determined.

Such a method for identifying a microbiota in a sample can include providing a sample, such as a skin sample, and detecting at least one microbiota in the sample. In some embodiments, the method can include preparing a nucleic acid sample including a molecular indicator of identity from at least one microbiota present in the sample and detecting the molecular indicator of identity.

For example, the method can involve preparing at least one nucleic acid sample by preparing a DNA sample. The molecular indicator of identity can be a polymorphic polynucleotide, such as an rRNA gene (for example, a 16S rRNA gene). The molecular indicator of identity can be detected by determining the nucleotide sequence of the polymorphic polynucleotide, such as the 16S rRNA gene, or a portion or subsequence thereof. Additional embodiments, for detecting the molecular indicator of identity can also include PCR with selective primers, quantitative PCR with selective primers, DNA-DNA hybridization, RNA-DNA hybridization, in situ hybridization, and combinations thereof. For example, the polymorphic polynucleotide can be detected by hybridization to a specific probe. In such an example, the specific probe hybridizes to a polymorphic target nucleic acid, such as a 16S rRNA gene. Optionally, the nucleic acid can be hybridized to at least one array including a plurality of specific probes, e.g., a plurality of specific probes, each of which identifies a species of bacteria. Detecting the molecular indicator of identity can also be accomplished using protein probes (such as antibodies) that bind to polymorphic target proteins, for example, polymorphic target proteins that identify the microbiota.

The relative abundance of one or more bacteria, such as *S. aureus*, can be measured in a sample from a subject. Relative abundance can refer to the commonality or rarity of an organism relative to other organisms in a defined location or community. For example, the relative abundance can be determined by generally measuring the presence of a particular organism compared to the total presence of organisms in a sample.

The relative abundance of bacteria can be measured directly or indirectly. Direct measurements can include culture based methods. Indirect measurements can include comparing the prevalence of a molecular indicator of identity, such as ribosomal RNA (rRNA) gene sequences, specific for an organism or group of organisms in relation to the overall sample.

In some embodiments, the relative abundance of microbiota, such as *S. aureus* and/or any type of bacteria, within the skin an individual subject can be calculated by measuring the ratio of one or more specific bacteria in a sample from an individual to obtain a microbiota profile of the subject. The relative abundance can be derived from the total abundance of bacteria present in a sample. The total abundance can refer to the total bacteria in a sample. A microbiota profile can refer to a representation, such as a graph, of the relative abundance of one or more microbiota in a subject or sample of skin from a subject.

Kits

Disclosed compositions can be provided as a component of a kit. The purified viable bacteria can be provided in a growth medium, lyophilized form, or as frozen cells. Thus, the kit can include a container including a therapeutically-effective amount of a purified viable bacteria and a metabolite.

In some embodiments, the kit can include the components needed to produce a pharmaceutical composition, such as one container including the bacteria and one container including a pharmaceutically-acceptable carrier for suspending the bacteria thereof. The pharmaceutically-acceptable carrier can be, for example, a buffered saline solution or a sucrose solution. In other embodiments, the kit can include a container including the bacteria, and a second container including a pharmaceutically-acceptable carrier, and a device, such as, but not limited to, a syringe, for measuring the pharmaceutically-acceptable carrier. In some embodiments, the kit includes a device, such as, but not limited to, a spray nozzle or a bandage, for topical application of the bacteria once it is suspended in the pharmaceutically-acceptable carrier.

Optionally, such a kit includes additional components including packaging, instructions and various other reagents, such as additional buffers or other therapeutic ingredients. The kit can include a container and a label or package insert on or associated with the container. Suitable containers can include, for example, bottles, vials, tubes, etc. The containers can be formed from a variety of materials, such as glass or plastic. The container can hold a composition including bacteria effective for treating atopic dermatitis. In some embodiments, the container can have a sterile access port. For example, the container can be an intravenous solution bag or a vial having a stopper pierceable by a hypodermic injection needle.

The label or package insert indicates that the composition can be used for treating the particular condition, such as atopic dermatitis. The label or package insert typically will further include instructions for use. The package insert typically includes instructions customarily included in commercial packages of therapeutic products that contain information about the indications, usage, dosage, administration, contraindications and/or warnings concerning the use of such therapeutic products. Non-limiting examples of instructions include information on the amount of the pharmaceutically-acceptable carrier to add to the vial containing the bacteria, instructions for suspending the bacteria in the pharmaceutically-acceptable carrier, and instructions for topical application to the skin. The application can be spraying on the skin, swabbing on the skin, or introducing the suspension onto a bandage for application to the skin.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Oral Pharmaceutical Composition for Treatment of Atopic Dermatitis

A pharmaceutical composition is designed for treatment of atopic dermatitis including a strain of *Roseomonas mucosa* described herein in the oral dosage form of a capsule.

Example 2: Rectal Pharmaceutical Composition for Treatment of Atopic Dermatitis

A pharmaceutical composition is designed for treatment of atopic dermatitis including a strain of *Roseomonas mucosa* described herein in the rectal dosage form of a suppository.

Example 3: Combination Therapies in Mouse Model for Atopic Dermatitis

MC903, a vitamin D analogue, induces an AD-like dermatitis when applied to mouse ears. For prevention studies, 1e7 CFU of gram negative bacteria is suspended in sterile PBS and dripped onto the mouse ears in 10 mcL of volume. Inoculations are initiated two days prior to MC903, and continued throughout the MC903 exposure. MC903 is placed first and the ethanol was allowed to evaporate for 2 to 5 minutes prior to placement of bacterial isolates. Ear thickness is measured on day 14. Half the mice are subject to co-inoculation of *S. aureus*, 1e6 CFU of the SAAS9 strain of *S. aureus* which is dripped onto the ear immediately prior to inoculation with the gram negative isolate. Treatment studies are performed by exposing mice to MC903 daily for 14 days and inoculating with 1e7 CFU total of strains provided in "Agent 1" (see Table 3) on days 13 to 15. Agents 2 and 3 are also administered on days 13 to 15. Ear thickness is measured and photos taken on day 21. Serum total IgE analysis: Serum was collected on day 14 of MC903. Serum is collected on day 14 of MC903 treatment and total IgE is determined. Bacterial strains are donor derived, where the donor subject is a human donor not having atopic dermatitis.

TABLE 3

Combination agent conditions.

| Condition | Agent 1 | Route for Agent 1 | Agent 2 | Route for Agent 2 | Agent 3 | Route for Agent 3 |
|---|---|---|---|---|---|---|
| 1 | *Roseomonas mucosa* | Topical | None | | None | |
| 2 | None | | Cyclosporine | Topical | None | |
| 3 | None | | None | | Desonide | Topical |
| 4 | None | | Cyclosporine | Oral | Desonide | Topical |
| 5 | *Roseomonas mucosa* | Topical | Cyclosporine | Oral | None | |
| 6 | *Roseomonas mucosa* | Topical | Cyclosporine | Oral | Desonide | Topical |
| 7 | *Roseomonas mucosa* | Topical | None | | Desonide | Topical |
| 8 | *Pseudomonas aeruginosa* | Topical | | | | |
| 9 | *Pseudomonas aeruginosa* | Topical | Cyclosporine | Oral | None | |
| 10 | *Pseudomonas aeruginosa* | Topical | Cyclosporine | Oral | Desonide | Topical |
| 11 | *Pseudomonas aeruginosa* | Topical | None | | Desonide | Topical |
| 12 | *Roseomonas mucosa* and *Pseudomonas aeruginosa* | Topical | None | | None | |
| 13 | *Roseomonas mucosa* and *Pseudomonas aeruginosa* | Topical | Cyclosporine | Oral | None | |
| 14 | *Roseomonas mucosa* and *Pseudomonas aeruginosa* | Topical | Cyclosporine | Oral | Desonide | Topical |
| 15 | *Roseomonas mucosa* and *Pseudomonas aeruginosa* | Topical | None | | Desonide | Topical |
| 16 | *Staphylococcus epidermis* | Topical | None | | None | |
| 17 | *Staphylococcus epidermis* | Topical | Cyclosporine | Oral | None | |
| 18 | *Staphylococcus epidermis* | Topical | Cyclosporine | Oral | Desonide | Topical |
| 19 | *Staphylococcus epidermis* | Topical | None | | Desonide | Topical |
| 20 | *Staphylococcus epidermis* and *Roseomonas mucosa* | Topical | None | | None | |
| 21 | *Staphylococcus epidermis* and *Roseomonas mucosa* | Topical | Cyclosporine | Oral | None | |
| 22 | *Staphylococcus epidermis* and *Roseomonas mucosa* | Topical | Cyclosporine | Oral | Desonide | Topical |
| 23 | *Staphylococcus epidermis* and *Roseomonas mucosa* | Topical | None | | Desonide | Topical |
| 24 | *Staphylococcus hominis* | Topical | None | | None | |
| 25 | *Staphylococcus hominis* | Topical | Cyclosporine | Oral | None | |
| 26 | *Staphylococcus hominis* | Topical | Cyclosporine | Oral | Desonide | Topical |
| 27 | *Staphylococcus hominis* | Topical | None | | Desonide | Topical |
| 28 | *Staphylococcus hominis* and *Roseomonas mucosa* | Topical | None | | None | |

TABLE 3-continued

Combination agent conditions.

| Condition | Agent 1 | Route for Agent 1 | Agent 2 | Route for Agent 2 | Agent 3 | Route for Agent 3 |
|---|---|---|---|---|---|---|
| 29 | *Staphylococcus hominis* *Roseomonas mucosa* | Topical | Cyclosporine | Oral | None | |
| 30 | *Staphylococcus hominis* *Roseomonas mucosa* | Topical | Cyclosporine | Oral | Desonide | Topical |
| 31 | *Staphylococcus hominis* *Roseomonas mucosa* | Topical | None | | Desonide | Topical |
| 32 | *Staphylococcus cohnii* | Topical | None | | None | |
| 33 | *Staphylococcus cohnii* | Topical | Cyclosporine | Oral | None | |
| 34 | *Staphylococcus cohnii* | Topical | Cyclosporine | Oral | Desonide | Topical |
| 35 | *Staphylococcus cohnii* | Topical | None | | Desonide | Topical |
| 36 | *Staphylococcus cohnii Roseomonas mucosa* | Topical | None | | None | |
| 37 | *Staphylococcus cohnii Roseomonas mucosa* | Topical | Cyclosporine | Oral | None | |
| 38 | *Staphylococcus cohnii Roseomonas mucosa* | Topical | Cyclosporine | Oral | Desonide | Topical |
| 39 | *Staphylococcus cohnii Roseomonas mucosa* | Topical | None | | Desonide | Topical |

Example 4: Treatment of Atopic Dermatitis Metabolite and a Microorganism

MC903, a vitamin D analogue, induces an AD-like dermatitis when applied to mouse ears. For prevention studies, 1e7 CFU of gram negative bacteria is suspended in sterile PBS and dripped onto the mouse ears in 10 mcL of volume. Inoculations are initiated two days prior to MC903, and continued throughout the MC903 exposure. MC903 is placed first, the ethanol was allowed to evaporate for 2-5 minutes prior to placement of bacterial isolates. Ear thickness is measured on day 14. Half the mice are subject to co-inoculation of *S. aureus*, 1e6 CFU of the SAAS9 strain of *S. aureus* which is dripped onto the ear immediately prior to inoculation with the gram negative isolate. Treatment studies is performed by exposing mice to MC903 daily for 14 days and inoculating with 1e7 CFU total of Agent 1 (see Table 4) on days 13-15. Agent 2 is administered on days 13-15. Ear thickness is measured and photos taken on day 21. Serum total IgE analysis: Serum was collected on day 14 of MC903. Serum is collected on day 14 of MC903 treatment and total IgE is determined. Agent 2 can be any of the metabolites listed in Table 1.

TABLE 4

Combination agent regimens.

| Condition | Agent 1 | Route for Agent 1 | Agent 2 | Route for Agent 2 |
|---|---|---|---|---|
| 1 | *Roseomonas mucosa* | Topical | None | |
| 2 | None | | Phosphatidylcholine 37:2 | Topical |
| 3 | *Roseomonas mucosa* | Topical | Phosphatidylcholine 37:2 | Topical |
| 4 | *Pseudomonas aeruginosa* | Topical | None | |
| 5 | *Pseudomonas aeruginosa* | Topical | Phosphatidylcholine 37:2 | Topical |
| 6 | *Roseomonas mucosa* and *Pseudomonas aeruginosa* | Topical | None | Topical |
| 7 | *Roseomonas mucosa* and *Pseudomonas aeruginosa* | Topical | Phosphatidylcholine 37:2 | Topical |
| 8 | *Staphylococcus epidermis* | Topical | None | |
| 9 | *Staphylococcus epidermis* | Topical | Phosphatidylcholine 37:2 | Topical |
| 10 | *Staphylococcus hominis* | Topical | None | |
| 11 | *Staphylococcus hominis* | Topical | Phosphatidylcholine 37:2 | Topical |
| 12 | *Staphylococcus cohnii* | Topical | None | |

TABLE 4-continued

Combination agent regimens.

| Condition | Agent 1 | Route for Agent 1 | Agent 2 | Route for Agent 2 |
|---|---|---|---|---|
| 13 | *Staphylococcus cohnii* | Topical | Phosphatidylcholine 37:2 | Topical |
| 14 | *Propionibacterium acnes* | Topical | None | |
| 15 | *Propionibacterium acnes* | Topical | Phosphatidylcholine 37:2 | Topical |
| 16 | *Moraxella osloensis* | Topical | None | |
| 17 | *Moraxella osloensis* | Topical | Phosphatidylcholine 37:2 | Topical |
| 18 | *Roseomonas mucosa* and *Pseudomonas aeruginosa* | Topical | None | |
| 19 | *Roseomonas mucosa* and *Pseudomonas aeruginosa* | Topical | Phosphatidylcholine 37:2 | Topical |
| 20 | *Roseomonas mucosa* and *Staphylococcus epidermis* | Topical | None | |
| 21 | *Roseomonas mucosa* and *Staphylococcus epidermis* | Topical | Phosphatidylcholine 37:2 | Topical |
| 22 | *Roseomonas mucosa* and *Staphylococcus hominis* | Topical | None | |
| 23 | *Roseomonas mucosa* and *Staphylococcus hominis* | Topical | Phosphatidylcholine 37:2 | Topical |
| 24 | *Roseomonas mucosa* and *Staphylococcus cohnii* | Topical | None | |
| 25 | *Roseomonas mucosa* and *Staphylococcus cohnii* | Topical | Phosphatidylcholine 37:2 | Topical |
| 26 | *Roseomonas mucosa* and *Propionibacterium acnes* | Topical | None | |
| 27 | *Roseomonas mucosa* and *Propionibacterium acnes* | Topical | Phosphatidylcholine 37:2 | Topical |
| 28 | *Roseomonas mucosa* and *Moraxella osloensis* | Topical | None | |
| 29 | *Roseomonas mucosa* and *Moraxella osloensis* | Topical | Phosphatidylcholine 37:2 | Topical |
| 30 | *Pseudomonas aeruginosa* and *Staphylococcus epidermis* | Topical | None | |
| 31 | *Pseudomonas aeruginosa* and *Staphylococcus epidermis* | Topical | Phosphatidylcholine 37:2 | Topical |
| 32 | *Pseudomonas aeruginosa* and *Staphylococcus hominis* | Topical | None | |
| 33 | *Pseudomonas aeruginosa* and *Staphylococcus hominis* | Topical | Phosphatidylcholine 37:2 | Topical |
| 34 | *Pseudomonas aeruginosa* and *Staphylococcus cohnii* | Topical | None | |
| 35 | *Pseudomonas aeruginosa* and *Staphylococcus cohnii* | Topical | Phosphatidylcholine 37:2 | Topical |
| 36 | *Pseudomonas aeruginosa* and *Propionibacterium acnes* | Topical | None | |
| 37 | *Pseudomonas aeruginosa* and *Propionibacterium acnes* | Topical | Phosphatidylcholine 37:2 | Topical |
| 38 | *Pseudomonas aeruginosa* and *Moraxella osloensis* | Topical | None | |
| 39 | *Pseudomonas aeruginosa* and *Moraxella osloensis* | Topical | Phosphatidylcholine 37:2 | Topical |
| 40 | *Moraxella osloensis* and *Staphylococcus epidermis* | Topical | None | |
| 41 | *Moraxella osloensis* and *Staphylococcus epidermis* | Topical | Phosphatidylcholine 37:2 | Topical |
| 42 | *Moraxella osloensis* and *Staphylococcus hominis* | Topical | None | |
| 43 | *Moraxella osloensis* and *Staphylococcus hominis* | Topical | Phosphatidylcholine 37:2 | Topical |
| 44 | *Moraxella osloensis* and *Staphylococcus cohnii* | Topical | None | |
| 45 | *Moraxella osloensis* and *Staphylococcus cohnii* | Topical | Phosphatidylcholine 37:2 | Topical |
| 46 | *Moraxella osloensis* and *Propionibacterium acnes* | Topical | None | |
| 47 | *Moraxella osloensis* and *Propionibacterium acnes* | Topical | Phosphatidylcholine 37:2 | Topical |

Example 5: Treatment of Atopic Dermatitis with Metabolite and Additional Therapeutic Agents MC903, a vitamin D analogue, induces an AD-like dermatitis when applied to mouse ears. For prevention studies, 1e7 CFU of gram negative bacteria is suspended in sterile PBS and dripped onto the mouse ears in 10 mcL of volume. Inoculations are initiated two days prior to MC903, and continued throughout the MC903 exposure. MC903 is placed first, the ethanol was allowed to evaporate for 2-5 minutes prior to placement of bacterial isolates. Ear thickness is measured on day 14. Half the mice are subject to co-inoculation of *S. aureus,* 1e6 CFU of the SAAS9 strain of *S. aureus* which is dripped onto the ear immediately prior to inoculation with the gram negative isolate. Treatment studies is performed by exposing mice to MC903 daily for 14 days and inoculating with 1e7 CFU total of Agent 1 (see Table 5) on days 13-15. Agents 2 and 3 are administered on days 13-15. Ear thickness is measured and photos taken on day 21. Serum total IgE analysis: Serum was collected on day 14 of MC903. Serum is collected on day 14 of MC903 treatment and total IgE is determined.

TABLE 5

Combination therapy regimen.

| Subject | Agent 1 | Route for Agent 1 | Agent 2 | Route for Agent 2 | Agent 3 | Route for Agent 3 |
|---|---|---|---|---|---|---|
| 1 | *Roseomonas mucosa* | Topical | None | | None | |
| 2 | None | | Desonide | Topical | None | |
| 3 | None | | None | | Phosphatidylcholine 37:2 | Topical |
| 4 | *Roseomonas mucosa* | Topical | Desonide | Topical | None | |
| 5 | *Roseomonas mucosa* | Topical | None | | Phosphatidylcholine 37:2 | Topical |
| 6 | None | | Desonide | Topical | Phosphatidylcholine 37:2 | Topical |
| 7 | *Roseomonas mucosa* | Topical | Desonide | Topical | Phosphatidylcholine 37:2 | Topical |
| 8 | *Pseudomonas aeruginosa* | Topical | None | | None | |
| 9 | *Pseudomonas aeruginosa* | Topical | Desonide | Topical | None | |
| 10 | *Pseudomonas aeruginosa* | Topical | Desonide | Topical | Phosphatidylcholine 37:2 | Topical |
| 11 | *Pseudomonas aeruginosa* | Topical | None | | Phosphatidylcholine 37:2 | Topical |
| 12 | *Roseomonas mucosa* and *Pseudomonas aeruginosa* | Topical | None | | None | |
| 13 | *Roseomonas mucosa* and *Pseudomonas aeruginosa* | Topical | Desonide | Topical | None | |
| 14 | *Roseomonas mucosa* and *Pseudomonas aeruginosa* | Topical | Desonide | Topical | Phosphatidylcholine 37:2 | Topical |
| 15 | *Roseomonas mucosa* and *Pseudomonas aeruginosa* | Topical | None | | Phosphatidylcholine 37:2 | Topical |
| 16 | *Staphylococcus epidermis* | Topical | None | | None | |
| 17 | *Staphylococcus epidermis* | Topical | Cyclosporine | Oral | None | |
| 18 | *Staphylococcus epidermis* | Topical | Cyclosporine | Oral | Desonide | Topical |
| 19 | *Staphylococcus epidermis* | Topical | None | | Desonide | Topical |
| 20 | *Staphylococcus epidermis Roseomonas mucosa* | Topical | None | | None | |
| 21 | *Staphylococcus epidermis Roseomonas mucosa* | Topical | Cyclosporine | Oral | None | |
| 22 | *Staphylococcus epidermis Roseomonas mucosa* | Topical | Cyclosporine | Oral | Desonide | Topical |
| 23 | *Staphylococcus epidermis Roseomonas mucosa* | Topical | None | | Desonide | Topical |
| 24 | *Staphylococcus hominis* | Topical | None | | None | |
| 25 | *Staphylococcus hominis* | Topical | Cyclosporine | Oral | None | |
| 26 | *Staphylococcus hominis* | Topical | Cyclosporine | Oral | Desonide | Topical |
| 27 | *Staphylococcus hominis* | Topical | None | | Desonide | Topical |
| 28 | *Staphylococcus hominis Roseomonas mucosa* | Topical | None | | None | |
| 29 | *Staphylococcus hominis Roseomonas mucosa* | Topical | Cyclosporine | Oral | None | |
| 30 | *Staphylococcus hominis Roseomonas mucosa* | Topical | Cyclosporine | Oral | Desonide | Topical |
| 31 | *Staphylococcus hominis Roseomonas mucosa* | Topical | None | | Desonide | Topical |

TABLE 5-continued

Combination therapy regimen.

| Subject | Agent 1 | Route for Agent 1 | Agent 2 | Route for Agent 2 | Agent 3 | Route for Agent 3 |
|---|---|---|---|---|---|---|
| 32 | *Staphylococcus cohnii* | Topical | None | | None | |
| 33 | *Staphylococcus cohnii* | Topical | Cyclosporine | Oral | None | |
| 34 | *Staphylococcus cohnii* | Topical | Cyclosporine | Oral | Desonide | Topical |
| 35 | *Staphylococcus cohnii* | Topical | None | | Desonide | Topical |
| 36 | *Staphylococcus cohnii Roseomonas mucosa* | Topical | None | | None | |
| 37 | *Staphylococcus cohnii Roseomonas mucosa* | Topical | Cyclosporine | Oral | None | |
| 38 | *Staphylococcus cohnii Roseomonas mucosa* | Topical | Cyclosporine | Oral | Desonide | Topical |
| 39 | *Staphylococcus cohnii Roseomonas mucosa* | Topical | None | | Desonide | Topical |

Example 6: Culturing Gram Negative Bacteria from Healthy Donors to Asses *S. aureus* Growth Inhibition Overgrowth and infection with *S. aureus* is both a contributor to, and consequence of, the immune imbalance and poor barrier function characteristic of atopic dermatitis. Multiple isolates of *S. aureus* are grown in the presence of the supernatant from cultures of healthy donor (HV)-derived bacteria or bacteria derived from a skin lesion of a subject having atopic dermatitis, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, or acne. *S. aureus* growth is assessed.

Co-inoculation of the cultured HV-derived bacteria or bacteria derived from a subject having a disease associated with skin dysbiosis with *S. aureus* are contacted to mouse ears and *S. aureus* yields are recorded. Lipid metabolite level for lysophosphatidylcholine (LPC) is also assessed. HV-derived bacteria referenced in Table 6 are assessed.

TABLE 6

Conditions.

| Condition | Agents |
|---|---|
| 1 | Saline |
| 2 | *Roseomonas mucosa* |
| 3 | *Pseudomonas aeruginosa* |
| 4 | *Staphylococcus epidermis* |
| 5 | *Staphylococcus hominis* |
| 6 | *Staphylococcus cohnii* |
| 7 | *Propionibacterium acnes* |
| 8 | *Moraxella osloensis* |
| 9 | *Roseomonas mucosa, Pseudomonas aeruginosa* |
| 10 | *Roseomonas mucosa, Staphylococcus epidermis* |
| 11 | *Roseomonas mucosa, Staphylococcus hominis* |
| 12 | *Roseomonas mucosa, Staphylococcus cohnii* |
| 13 | *Roseomonas mucosa, Propionibacterium acnes* |
| 14 | *Roseomonas mucosa, Moraxella osloensis* |
| 15 | *Pseudomonas aeruginosa, Staphylococcus epidermis* |
| 16 | *Pseudomonas aeruginosa, Staphylococcus hominis* |
| 17 | *Pseudomonas aeruginosa, Staphylococcus cohnii* |
| 18 | *Pseudomonas aeruginosa, Propionibacterium acnes* |

TABLE 6-continued

Conditions.

| Condition | Agents |
|---|---|
| 19 | *Pseudomonas aeruginosa, Moraxella osloensis* |
| 20 | *Moraxella osloensis, Staphylococcus epidermis* |
| 21 | *Moraxella osloensis, Staphylococcus hominis* |
| 22 | *Moraxella osloensis, Staphylococcus cohnii* |
| 23 | *Moraxella osloensis, Propionibacterium acnes* |

Example 7: Culturing Gram Negative Bacteria from Healthy Donors to Induce Innate Immunity in Humans To measure in vivo human cutaneous immune reactivity to bacteria described herein, human foreskin-derived primary keratinocytes (KC) are infected with isolates of live healthy donor-derived bacteria or bacteria derived from a skin lesion of a subject having atopic dermatitis, eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, or acne. 20-24 hours after infection, KCs exposed to HV-bacteria are screened for a relative increase compared to those exposed to bacteria derived from the subject having the disease associated with skin dysbiosis for increase in mRNA levels for defensin β4A, CYP27b1 (a vitamin D converting enzyme), the vitamin D receptor (VDR), and the antimicrobial peptide cathelicidin. HV-derived bacteria referenced in Table 3 are assessed.

Example 8: Culturing Gram Negative Bacteria from Healthy Donors to Assess Barrier Function in Mice The loss of barrier function in AD causes dry, itchy skin due to trans-epidermal water loss (TEWL) and cutaneous sensitization to antigens. For a subset of subjects, this barrier defect is associated with dysfunction in the tight-junction protein filaggrin. Isolates of live HV-derived bacteria or bacteria derived from a skin lesion of a subject having atopic dermatitis are topically applied to healthy mouse ears, which are subsequently assessed for enhanced transcript levels of filaggrin, ear thickness change, and TWEL. HV-derived bacteria referenced in Table 3 are assessed. Combination agent delivery as described in Table 5 is also assessed.

Example 9: Culturing Gram Negative Bacteria from Healthy Donors to Assess Outcomes in a Mouse Model of Atopic Dermatitis MC903, a vitamin D analogue, induces an AD-like dermatitis when applied to mouse ears. Isolates of live HV-derived bacteria or bacteria derived from a subject having atopic dermatitis are topically applied to healthy mouse ears prior to administration of MC903. Ear thickness, serum IgE induction, mRNA levels (for filaggrin, defensin β4A, CYP27b1, VDR, and cathelicidin), are compared before and after MC903 administration. HV-derived bacteria referenced in Table 3 are assessed. Combination agent delivery as described in Table 5 is also assessed.

Example 10: Generation and Characterization of a Pharmaceutical Formulation of R. mucosa from Healthy Volunteers Three isolates of R. mucosa from 3 human healthy volunteers (HVs) are grown in minimal media (R2A broth, Teknova; or Hanks Buffered Salt Solution, HBSS, Gibco) for 24-48 hours. Isolates are selected based on their ability to inhibit the growth of S. aureus, activate vitamin D pathways in human keratinocytes, and improve outcomes in mouse models of AD. The isolates are referenced as RM-A, RM-B, and RM-C. Genomic sequencing is performed on all strains to verify that no transmittable, clinically significant antibiotic resistance genes were present. The bacterial cells are washed 3 times in PBS (Gibco) and resuspended into 10%-15% sucrose in water for a concentration of 109 CFU/ml. Serial dilutions are performed in 10%-15% sucrose to generate stocks of 104, 105, and 106 per ml. Aliquots of diluted bacterial samples are plated on R2A agar (Remel) and incubated at 32° C. for 48-72 hours to enumerate prelyophilization CFU concentration. Eight hundred microliters (adult) or 1.5 ml (pediatric) of bacterial solution is frozen in 1.5-ml amber glass vials (Wheaton; adult) or a 3-ml self-contained sprayer system (Discount Vials; pediatrics) prior to lyophilization (Labconco). Vials/sprayers are sealed, labeled, and stored at −70° C. until dispensed to the patients.

Genomes from the three isolates of R. mucosa have regions of sequence specific to each of the three isolates, as show in in Table 7 (bases specific to each strain are in bold and underlined).

TABLE 7

| Strain | Nucleic Acid | SEQ ID NO: |
|---|---|---|
| RM-A | CGGCGGCGGACAGCCCCTCCACCCATCCTCGCCGAG CCCGATGATGCTAA | 1 |
| RM-B | CGGCGGCGGACAGCCCCTCCACTCCACCTCGCCGAGC CCGATGATGCTAA | 2 |
| RM-C | CGGCGGCGGACAGCCCCTCCACCCCGTCCTCGCCGAG CCCGATGATGCTAA | 3 |

Primers designed to amplify the region where strain specific variation is identified. A Custom TaqMan® SNP Genotyping Assays, Non-human, SM kit and protocol is used to perform an analysis for detection of each strain. Briefly, DNA from each isolate is subjected to PCR where the primers were SEQ ID NO: 4 (CACCGGACAGCAGGCT), and SEQ ID NO: 5 (GCGGTGGCTTAGCATCATC). Amplification products are subjected to an allelic discrimination assay. In a first comparison, the following reporters are used: SEQ ID NO: 6 (CACCCCATCCTCG) and SEQ ID NO: 7 (CACCCCGTCCTCG). This is an A/G allelic discrimination assay. In a second comparison, the following reporters are used: SEQ ID NO: 8 (CCCTCCACCCCATCCT) and SEQ ID NO: 9 (CCCTCCACTCCATCCT). This is a T/C allelic discrimination assay.

Example 11: MC903-Induced Atopic Dermatitis Model in Mice

Balb/c male mice are subject to a model for induction of atopic dermatitis. MC903 is dissolved in 100% ethanol and topically applied on mouse ears (2 and 4 nmol in 25 μl per ear) for 14 days. A control group is treated with ethanol only. Gradual induction of lesions in the ear in mice is monitored by scoring for ear thickness, appearance of scars and redness. Every other day in-life observations are done from Day 5 to Day 15, and ears are collected on Day 15 for histopathological evaluation of the disease. The route of administration is oral gavage, twice daily. Subjects are divided as summarized below in Table 8.

TABLE 8

| Group | Dose (mg/kg) | Population N |
|---|---|---|
| 1. Control Naive (optional) | 0 | 10 |
| 2. Vehicle | 0 | 10 |
| 3. MC903, Dose 1 | TBD | 10 |
| 4. MC903, Dose 2 | TBD | 10 |
| 5. MC903, Dose 1 + Positive control (Clobetasol cream, 0.05%) | 62.5 mg/day | 10 |
| 6. Positive control (Clobetasol cream, 0.05%) | 62.5 mg/day | 10 |

The acclimation period before start of treatment is at least five days. Body weight is measured before start of model induction and then before each dosing. Baseline thickness of the ear is taken by digital caliper and animals are randomized into different treatment groups. From Day 5 to Day 15, assessment of ear thickness, erythema score and skin scaling score are done. On Day 15, the right ear is collected from all animals, and fixed in 10% NBF for histopathological assessment. The left ear is collected and snap frozen for future gene or cytokine analysis. Spleen and lymph nodes are also collected. Terminal serum is collected and kept for potential IgE antibody analysis. H&E staining of right ears (one slide/animal) is performed, histological evaluation of Epidermal thickness is performed using the Image-Pro system. Subjects are dosed with single and combination therapies as described in Example 3, Table 3.

Example 12: Imiquimod (IMQ)-Induced Psoriasis Model in Mice

Balb-c male mice are subject to a model for psoriasis. Animals receive 62.5 mg of 5% IMQ cream topically on the back skin (we can perform this model using ears if there is limitation for test item availability) once daily from Day 1 to Day 11. IMQ causes gradual induction of psoriasis-like lesions in the skin in mice as evidenced by increase in thickness, appearance of scars and redness. Daily in-life observations are done from Day 2 to Day 12, and back skin is collected on Day 12 for possible histopathological evaluation of the disease. Dosing regimen is to start 3 days prior to first IMQ application on Day −3. Administration is daily by topical administration. Subjects are divided as summarized below in Table 9.

TABLE 9

Test System:

| Group | Dose (mg/kg) | Population N |
|---|---|---|
| 1. Control Naive (optional) | 0 | 10 |
| 2. IMQ + Vehicle | 0 | 10 |
| 3. IMQ + TI, 1 | TBD | 10 |
| 4. IMQ + TI, 2 | TBD | 10 |
| 5. IMQ + Positive control (Clobetasol cream, 0.05%) | 62.5 mg/day | 10 |

Subjects are given an acclimation period of at least 5 days before initiation of treatment. Body weight is measured once before start of IMQ application and then before each dosing. On Day 0, baseline thickness of the back skin is taken by a digital caliper and animals are randomized into different treatment groups. From Day 2 to Day 12, daily assessment of back skin thickness, skin erythema score and skin scaling score are done. Skin samples collected from all animals at termination and analysis for IL13, TNFa, MIP-1a, G-CSF and IL-17 (5plex) using a Bio-Rad kit. Terminal Procedures: On Day 12, back skin is collected from all animals, and fixed in 10% NBF for histopathological assessment. If required, skin samples are snap frozen for cytokine analysis. Terminal blood plasma/serum is collected. H&E staining of back skin and/or ear sections is performed (one slide/animal). Epidermal thickness, Parakeratosis, Acanthosis and Inflammatory infiltrate scorings, and a Composite score are performed. Subjects are dosed with single and combination therapies as described in Example 3, Table 3.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treatment of a skin condition associated with inflammation or barrier dysfunction, comprising:
    administering to a subject in need thereof:
        a purified phosphatidylethanolamine;
        at least one strain of a live, purified gram negative bacteria; and
        at least one strain of live, purified gram positive bacteria,
    wherein the administering provides for reduction of a skin condition associated with inflammation or barrier dysfunction in the subject.

2. The method of claim 1, wherein the phosphatidylethanolamine comprises phosphatidylethanolamine 14:0/20:1, phosphatidylethanolamine 22:1/14:1, or phosphatidylethanolamine 36:2.

3. The method of claim 1, wherein the purified phosphatidylethanolamine is in a topical dosage form.

4. The method of claim 3, wherein the topical dosage form is a liquid, cream, gel, or foam.

5. The method of claim 1, wherein the live, purified gram negative bacteria comprises a species is of the genus *Pseudomonas, Pantoea, Moraxella, Roseomonas,* or *Vitreoscilla*.

6. The method of claim 1, wherein the live, purified gram negative bacteria comprises *Roseomonas mucosa, Pseudomonas aeruginosa,* or *Moraxella osloensis*.

7. The method of claim 1, wherein the live, purified gram negative bacteria is *Roseomonas mucosa*.

8. The method of claim 1, wherein the live, purified gram negative bacteria is *Roseomonas mucosa,* and comprises a nucleic acid sequence of SEQ ID NO: 1, SEQ ID NO: 2, or SEQ ID NO: 3.

9. The method of claim 1, wherein the live, purified gram positive bacteria comprises *Staphylococcus epidermis, Staphylococcus cohnii,* or *Staphylococcus hominis*.

10. The method of claim 1, wherein the live, purified gram negative bacteria is in a topical dosage form.

11. The method of claim 10, wherein the topical dosage form is a liquid, cream, gel, or foam.

12. The method of claim 1, wherein the purified phosphatidylethanolamine and the live, purified gram negative bacteria are concurrently administered.

13. The method of claim 1, wherein the purified phosphatidylethanolamine, the live, purified gram negative bacteria, and wherein the live, purified gram positive bacteria are present together in a pharmaceutical composition.

14. The method of claim 1, wherein the purified phosphatidylethanolamine, the live, purified gram negative bacteria, and wherein the live, purified gram positive bacteria are present in separate pharmaceutical compositions.

15. The method of claim 1, wherein the skin condition associated with inflammation or barrier dysfunction is eczema, allergic eczema, flexural eczema, infantile eczema, nummular eczema, discoid lupus, prurigo Besnier, psoriasis, vitiligo, dermatitis, atopic dermatitis, perioral dermatitis, neurodermatitis, seborrheic dermatitis, rosacea, or acne.

16. The method of claim 13, wherein the pharmaceutical composition is in a topical dosage form.

17. The method of claim 16, wherein the topical dosage form is a liquid, cream, gel, or foam.

* * * * *

SEQUENCE LISTING

<160> NUMBER OF SEQ ID NOS: 9

<210> SEQ ID NO 1
<211> LENGTH: 51
<212> TYPE: DNA
<213> ORGANISM: Roseomonas mucosa

<400> SEQUENCE: 1
cggcggcgga cagcccctcc acccatcct cgccgagccc gatgatgcta a       51

<210> SEQ ID NO 2
<211> LENGTH: 50
<212> TYPE: DNA
<213> ORGANISM: Roseomonas mucosa

<400> SEQUENCE: 2
cggcggcgga cagcccctcc actccacctc gccgagcccg atgatgctaa        50

<210> SEQ ID NO 3
<211> LENGTH: 51
<212> TYPE: DNA
<213> ORGANISM: Roseomonas mucosa

<400> SEQUENCE: 3
cggcggcgga cagcccctcc acccgtcct cgccgagccc gatgatgcta a       51

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
caccggacag caggct                                                  16

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggtggctt agcatcatc                                               19

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caccccatcc tcg                                                     13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caccccgtcc tcg                                                     13

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccctccaccc catcct                                                  16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccctccactc catcct                                                  16
```